United States Patent
Schneyer

(10) Patent No.: US 10,941,195 B2
(45) Date of Patent: Mar. 9, 2021

(54) ANTI-FOLLISTATIN-LIKE 3 ANTIBODIES AND TREATMENT OF DIABETES

(71) Applicant: Fairbanks Pharmaceuticals, Inc., Concord, MA (US)

(72) Inventor: Alan Schneyer, Concord, MA (US)

(73) Assignee: FAIRBANKS PHARMACEUTICALS, INC., Concord, MA (US)

(*) Notice: Subject to any disclaimer, the term of this patent is extended or adjusted under 35 U.S.C. 154(b) by 0 days.

(21) Appl. No.: 16/337,267

(22) PCT Filed: Oct. 4, 2017

(86) PCT No.: PCT/US2017/055214
§ 371 (c)(1),
(2) Date: Mar. 27, 2019

(87) PCT Pub. No.: WO2018/067754
PCT Pub. Date: Apr. 12, 2018

(65) Prior Publication Data
US 2020/0190171 A1 Jun. 18, 2020

Related U.S. Application Data

(60) Provisional application No. 62/404,169, filed on Oct. 4, 2016.

(51) Int. Cl.
| | |
|---|---|
| *A61K 39/395* | (2006.01) |
| *C07K 16/18* | (2006.01) |
| *A61P 3/10* | (2006.01) |
| *A61K 39/00* | (2006.01) |

(52) U.S. Cl.
CPC ............... *C07K 16/18* (2013.01); *A61P 3/10* (2018.01); *A61K 2039/505* (2013.01); *C07K 2317/24* (2013.01); *C07K 2317/33* (2013.01); *C07K 2317/565* (2013.01); *C07K 2317/76* (2013.01)

(58) Field of Classification Search
None
See application file for complete search history.

(56) References Cited

U.S. PATENT DOCUMENTS 8,895,011 B2 * 11/2014 Kadowaki ............ A61K 31/00
424/172.1
2013/0156793 A1 6/2013 Kadowaki et al.

FOREIGN PATENT DOCUMENTS

WO 2018/067754 A1 4/2018

OTHER PUBLICATIONS

Anonymous, "Human Follistatin-related Gene Protein/FLRG Antibody MAB1288: R&D Systems," R&D Systems Online Catalog, 3 pages; retrieved from Internet URL: https://www.rndsystems.com/products/human-follistatin-related-gene-protein-flrg-antibody-206714_mab1288?utm . . . [retreived on Jan. 2, 2018].

Brown, M.L. et al., "Activin Enhances α- to β-Cell Transdifferentiation as a Source for β-Cells in Male FSTL3 Knockout Mice," Endocrinology, vol. 157; No. 3; 1043-1054 (2016).

Cash, J.N. et al., "Structure of Myostatin Follistatin-like 3 N-Terminal Domains of Follistatin-Type Molecules exhibit Alternate Modes of Binding," Journal of Biological Chemistry, vol. 287; No. 2; 1043-1053 (2012).

Nanda, S. et al., "Prediction of gestational diabetes mellitus by maternal factors and biomarkers at 11 to 13 weeks," Prenatal Diagnosis, vol. 31; 135-141 (2010).

N.N., "Human Follistatin-related geneprotein/FLRG antibody AF1288," R&D Systems Online Catalog, 2 pages; retrieved from Internet URL: https://resources.rndsystems.com/pdfs/datasheets/af1288.pdf [retrieved on Jan. 2, 2018].

Notification of International Search Report and Written Opinion for International Application No. PCT/US2017/055214, entitled: "Anti-FSTL3 Antibodies and Uses Thereof," dated Jan. 30, 2018.

International Preliminary Report on Patentability for International Application No. PCT/US2017/055214, titled: "Anti-FSTL3 Antibodies and Uses Thereof," dated Apr. 9, 2019.

* cited by examiner

*Primary Examiner* — Christine J Saoud
(74) *Attorney, Agent, or Firm* — Hamilton, Brook, Smith & Reynolds, P.C.

(57) ABSTRACT

The present invention provides antibodies and antigen binding fragments thereof that bind to human Follistatin-Like-3 (FSTL3) protein, compositions comprising such antibodies, and methods of making and using such antibodies.

14 Claims, 11 Drawing Sheets

Specification includes a Sequence Listing.

Activin A activity in CAGA-Luc Assay

Inhibition of Activin A Signaling By hFSTL3

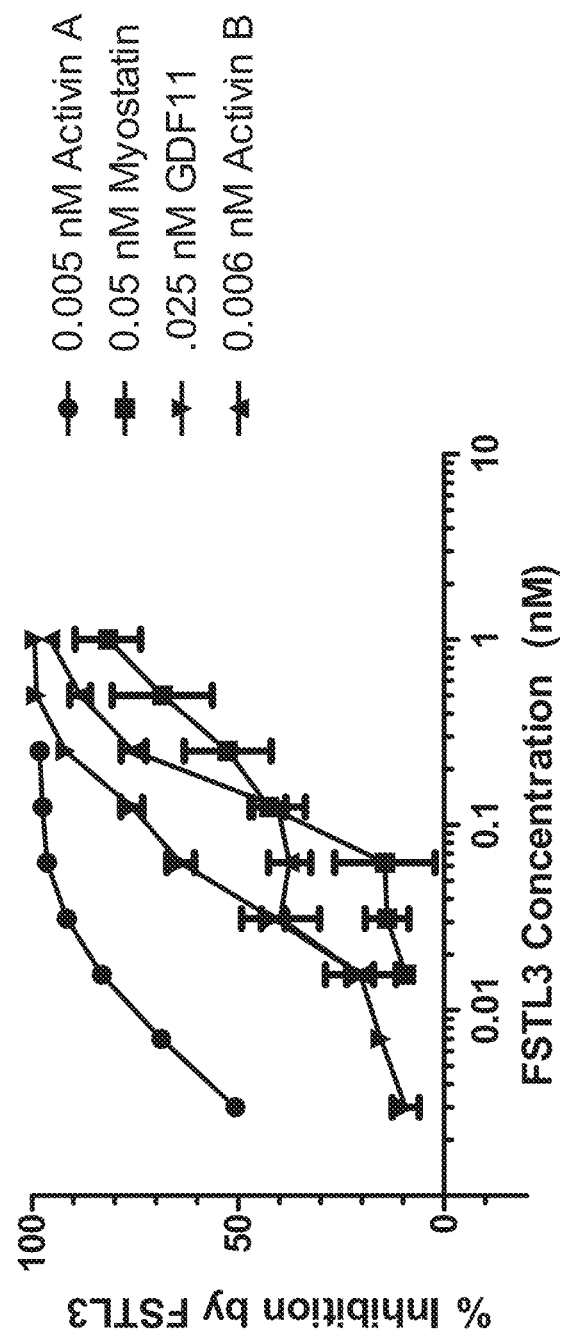

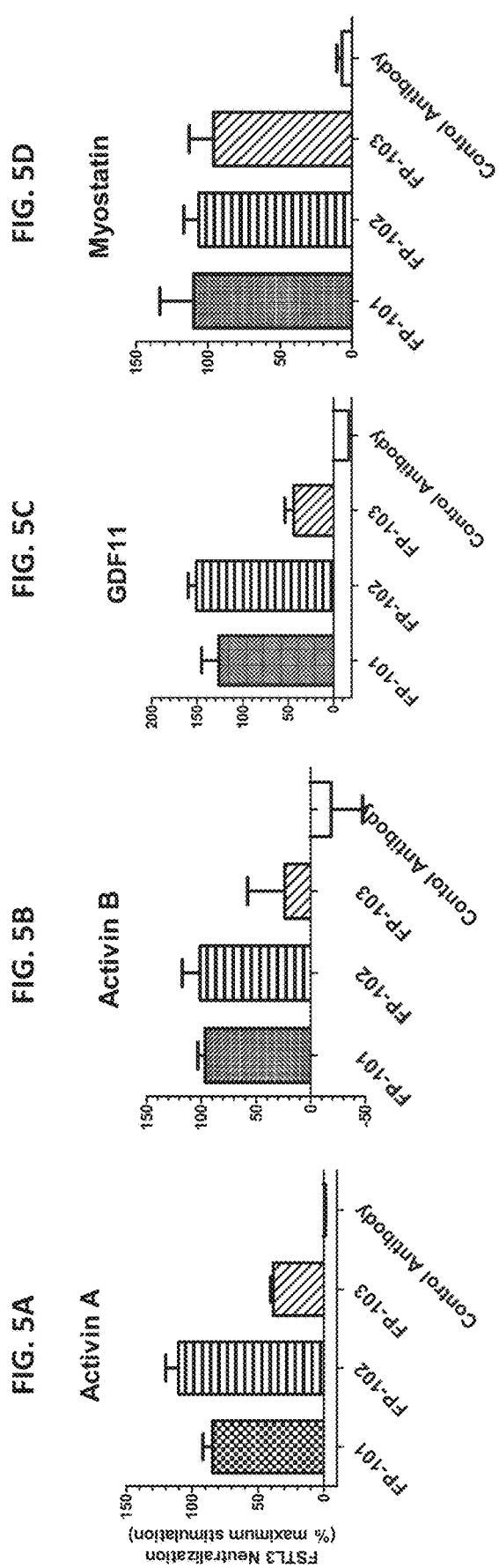

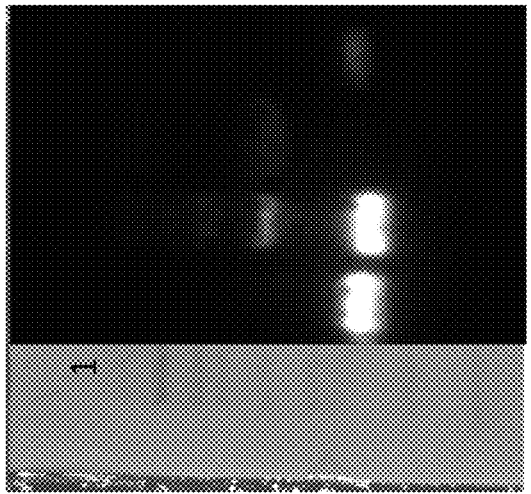
FIG. 6A FP-101
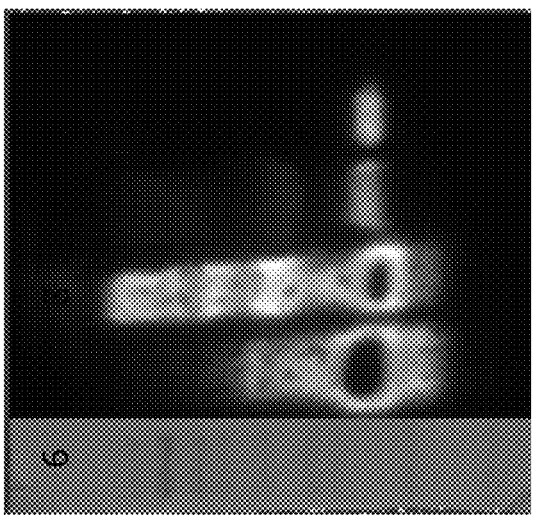
FIG. 6B FP-102
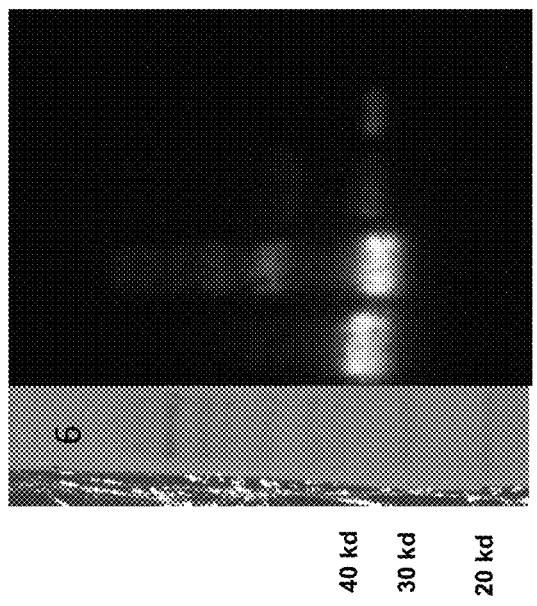
FIG. 6C FP-103

```
                              SEQUENCE LISTING

<160> NUMBER OF SEQ ID NOS: 20

<210> SEQ ID NO 1
<211> LENGTH: 632
<212> TYPE: DNA
<213> ORGANISM: ARTIFICIAL SEQUENCE
<220> FEATURE:
<223> OTHER INFORMATION: Nucleic acid encoding antibody variable domain
<220> FEATURE:
<221> NAME/KEY: misc_feature
<222> LOCATION: (632)..(632)
<223> OTHER INFORMATION: n is a, c, g, or t

<400> SEQUENCE: 1
gaggttcagc tgcagcagtc tgcagctgaa ctggcaagac ctggggcctc agtgaagatg     60
tcctgcaagg cttctggcta ctcctttaca acctacacga tgcactgggt aaaacagagg    120
cctggacagg gtctggaatg gattggatac attcatccta gcagtggata tactgatcac    180
attcagaagt tcaaggacaa gaccatattg actgcggaca atcctccag cacagcctac    240 atgcaactga acagcctaac atctgaggac tctgcggtct attactgtgc aagattggac    300
tatggctact ggggccaagg caccactctc acagtctcct cagccaaaac gacaccccca    360
tctgtctatc cactggcccc tggatctgct gcccaaacta actccatggt gaccctggga    420
tgcctggtca agggctattt ccctgagcca gtgacagtga cctggaactc tggatccctg    480
tccagcggtg tgcacaccttc ccagctgtc ctgcagtctg acctctacac tctgagcagc    540
tcagtgactg tcccctccag cacctggccc agcgagaccg tcacctgcaa cgttgcccac    600
ccggccagca gcaccaaggt ggacaagaaa an                                   632

<210> SEQ ID NO 2
<211> LENGTH: 224
<212> TYPE: PRT
<213> ORGANISM: ARTIFICIAL SEQUENCE
<220> FEATURE:
<223> OTHER INFORMATION: Antibody Variable domain

<400> SEQUENCE: 2

Glu Val Gln Leu Gln Gln Ser Ala Ala Glu Leu Ala Arg Pro Gly Ala
1               5                   10                  15

Ser Val Lys Met Ser Cys Lys Ala Ser Gly Tyr Ser Phe Thr Thr Tyr
                20                  25                  30

Thr Met His Trp Val Lys Gln Arg Pro Gly Gln Gly Leu Glu Trp Ile
            35                  40                  45

Gly Tyr Ile His Pro Ser Ser Gly Tyr Thr Asp His Ile Gln Lys Phe
        50                  55                  60

Lys Asp Lys Thr Ile Leu Thr Ala Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Leu Asp Tyr Gly Tyr Trp Gly Gln Gly Thr Thr Leu Thr Val
            100                 105                 110

Ser Ser Ala Lys Thr Thr Pro Pro Ser Val Tyr Pro Leu Ala Pro Gly
        115                 120                 125
```

```
Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Asp Tyr Lys Asp Asp Asp Lys Phe Tyr Ser Val Thr
    210                 215                 220

<210> SEQ ID NO 3
<211> LENGTH: 9
<212> TYPE: PRT
<213> ORGANISM: ARTIFICIAL SEQUENCE
<220> FEATURE:
<223> OTHER INFORMATION: Antibody CDR

<400> SEQUENCE: 3

Tyr Ser Phe Thr Thr Tyr Thr Met His
1               5

<210> SEQ ID NO 4
<211> LENGTH: 15
<212> TYPE: PRT
<213> ORGANISM: ARTIFICIAL SEQUENCE
<220> FEATURE:
<223> OTHER INFORMATION: Antibody CDR

<400> SEQUENCE: 4

Trp Ile Gly Tyr Ile His Pro Ser Ser Gly Tyr Thr Asp His Ile
1               5                   10                  15

<210> SEQ ID NO 5
<211> LENGTH: 6
<212> TYPE: PRT
<213> ORGANISM: ARTIFICIAL SEQUENCE
<220> FEATURE:
<223> OTHER INFORMATION: Antibody CDR

<400> SEQUENCE: 5

Arg Leu Asp Tyr Gly Tyr
1               5

<210> SEQ ID NO 6
<211> LENGTH: 588
<212> TYPE: DNA
<213> ORGANISM: ARTIFICIAL SEQUENCE
<220> FEATURE:
<223> OTHER INFORMATION: Nucleic acid encoding antibody variable domain
<220> FEATURE:
<221> NAME/KEY: misc_feature
<222> LOCATION: (583)..(583)
<223> OTHER INFORMATION: n is a, c, g, or t

<400> SEQUENCE: 6
actcaaactc cactctccct gcctgtcagt cttggagatc aagcctccat ctcttgcaga      60
tctagtcaga gcattgtaca tagtaatgga aacacctatt tagaatggta cctgcagaaa    120
ccaggccagt ctccaaagct cctgatctac aaagtttcca accgattttc tggggtccca    180
gacaggttca ctggcagtgg atcagggaca gatttcacac tcaagatcag cagagtggag    240
```

```
gctgcggatc tgggagttta ttactgcttt caaagttcac atattcctcc gacgttcggt    300
ggaggcacca agctggaaat caaacgggct gatgctgcac caactgtatc catcttccca    360
ccatccagtg agcagttaac atctggaggt gcctcagtcg tgtgcttctt gaacaacttc    420
taccccaaag acatcaatgt caagtggaag attgatggca gtgaacgaca aaatggcgtc    480
ctgaacagtt ggactgatca ggacagcaaa gacagcacct acagcatgag cagcaccctc    540
acgttgacca aggacgagta tgaacgacat aacagctata ccngtgag                 588
```

<210> SEQ ID NO 7
<211> LENGTH: 215
<212> TYPE: PRT
<213> ORGANISM: ARTIFICIAL SEQUENCE
<220> FEATURE:
<223> OTHER INFORMATION: Antibody Variable domain
<220> FEATURE:
<221> NAME/KEY: misc_feature
<222> LOCATION: (199)..(199)
<223> OTHER INFORMATION: Xaa can be any naturally occurring amino acid

<400> SEQUENCE: 7

Asp Ile Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Ala Asp Leu Gly Val Tyr Tyr Cys Phe Gln Ser
                85                  90                  95

Ser His Ile Pro Pro Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Xaa Glu Ala Thr His Lys Thr Ser Thr Ser
        195                 200                 205

Pro Ile Val Lys Ser Phe Asn
    210                 215

<210> SEQ ID NO 8
<211> LENGTH: 13
<212> TYPE: PRT
<213> ORGANISM: ARTIFICIAL SEQUENCE
<220> FEATURE:
<223> OTHER INFORMATION: Antibody CDR

<400> SEQUENCE: 8

Gln Ser Ile Val His Ser Asn Gly Asn Thr Tyr Leu Glu
1               5                   10

<210> SEQ ID NO 9
<211> LENGTH: 11
<212> TYPE: PRT
<213> ORGANISM: ARTIFICIAL SEQUENCE
<220> FEATURE:
<223> OTHER INFORMATION: Antibody CDR

<400> SEQUENCE: 9

Leu Leu Ile Tyr Lys Val Ser Asn Arg Phe Ser
1               5                   10

<210> SEQ ID NO 10
<211> LENGTH: 8
<212> TYPE: PRT
<213> ORGANISM: ARTIFICIAL SEQUENCE
<220> FEATURE:
<223> OTHER INFORMATION: Antibody CDR

<400> SEQUENCE: 10

Phe Gln Ser Ser His Ile Pro Pro
1               5

<210> SEQ ID NO 11
<211> LENGTH: 608
<212> TYPE: DNA
<213> ORGANISM: ARTIFICIAL SEQUENCE
<220> FEATURE:
<223> OTHER INFORMATION: Nucleic acid encoding antibody variable domain

<400> SEQUENCE: 11

```
atgcaggtta agctgcagca gcctgggggct gaactggtga agcctggggc ttcagtgaag    60
ctgtcctgca aggcttctgg ctacaccttc accagctact ggatgcactg ggtgaatcag   120
aggcctggac aaggccttga gtggattgga gagattaatc ctggcaacgg tcgtactaac   180
tacaatgaga agttcaagag caaggccaca ctgactgtag acaaatcctc cagcacagcc   240
tacatgcaac tcagcagcct gacatctgag gactctgcgg tctatttctg cgcaagatgg   300
ttgctacccc ggggggcctat ggactactgg ggtcaaggaa cctcagtcac cgtctcctca   360
gccaaaacga cacccccatc tgtctatcca ctggcccctg gatctgctgc ccaaactaac   420
tccatggtga ccctgggatg cctggtcaag ggctatttcc ctgagccagt gacagtgacc   480
tggaactctg gatccctgtc cagcggtgtg cacaccttcc cagctgtcct gcagtctgac   540
ctctacactc tgagcagctc agtgactgtc ccctccagca cctggcccag cgagaccgtc   600
acctgcaa                                                           608
```

<210> SEQ ID NO 12
<211> LENGTH: 203
<212> TYPE: PRT
<213> ORGANISM: ARTIFICIAL SEQUENCE
<220> FEATURE:
<223> OTHER INFORMATION: Antibody Variable domain

<400> SEQUENCE: 12

Met Gln Val Lys Leu Gln Gln Pro Gly Ala Glu Leu Val Lys Pro Gly
1               5                   10                  15

Ala Ser Val Lys Leu Ser Cys Lys Ala Ser Gly Tyr Thr Phe Thr Ser
                20                  25                  30

Tyr Trp Met His Trp Val Asn Gln Arg Pro Gly Gln Gly Leu Glu Trp
        35                  40                  45

```
Ile Gly Glu Ile Asn Pro Gly Asn Gly Arg Thr Asn Tyr Asn Glu Lys
        50                  55                  60

Phe Lys Ser Lys Ala Thr Leu Thr Val Asp Lys Ser Ser Ser Thr Ala
 65                  70                  75                  80

Tyr Met Gln Leu Ser Ser Leu Thr Ser Glu Asp Ser Ala Val Tyr Phe
                85                  90                  95

Cys Ala Arg Trp Leu Leu Pro Arg Gly Pro Met Asp Tyr Trp Gly Gln
               100                 105                 110

Gly Thr Ser Val Thr Val Ser Ser Ala Lys Thr Thr Pro Pro Ser Val
           115                 120                 125

Tyr Pro Leu Ala Pro Gly Ser Ala Ala Gln Thr Asn Ser Met Val Thr
           130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
               165                 170                 175

Leu Gln Ser Asp Leu Tyr Thr Leu Ser Ser Ser Val Thr Val Pro Ser
           180                 185                 190

Ser Thr Trp Pro Ser Glu Thr Val Thr Cys Asn
           195                 200
```

<210> SEQ ID NO 13
<211> LENGTH: 9
<212> TYPE: PRT
<213> ORGANISM: ARTIFICIAL SEQUENCE
<220> FEATURE:
<223> OTHER INFORMATION: Antibody CDR

<400> SEQUENCE: 13

```
Tyr Thr Phe Thr Ser Tyr Trp Met His
 1               5
```

<210> SEQ ID NO 14
<211> LENGTH: 14
<212> TYPE: PRT
<213> ORGANISM: ARTIFICIAL SEQUENCE
<220> FEATURE:
<223> OTHER INFORMATION: Antibody CDR

<400> SEQUENCE: 14

```
Trp Ile Gly Glu Ile Asn Pro Gly Asn Gly Arg Thr Asn Tyr
 1               5                  10
```

<210> SEQ ID NO 15
<211> LENGTH: 11
<212> TYPE: PRT
<213> ORGANISM: ARTIFICIAL SEQUENCE
<220> FEATURE:
<223> OTHER INFORMATION: Antibody CDR

<400> SEQUENCE: 15

```
Arg Trp Leu Leu Pro Arg Gly Pro Met Asp Tyr
 1               5                  10
```

<210> SEQ ID NO 16
<211> LENGTH: 583
<212> TYPE: DNA
<213> ORGANISM: ARTIFICIAL SEQUENCE
<220> FEATURE:
<223> OTHER INFORMATION: Nucleic acid encoding antibody variable domain

<400> SEQUENCE: 16

```
atgtccacat cagtaggaga cagggtcagc gtcacctgca aggccagtca gaatgtgggt    60
actaatgtag cctggtatca acagaaacca gggcaatctc ctcaaggact gatttactcg   120
gcatcctacc ggtacagtgg agtccctgat cgcttcacag gcagtggatc tgggacagat   180
ttcactctca ccatcagcaa tgtgcagtct gaagacttgg cagagtattt ctgtcagcaa   240
tataacagct atccgctcac gttcggtgct gggaccaagc tggagctgaa acgggctgat   300
gctgcaccaa ctgtatccat cttcccacca tccagtgagc agttaacatc tggaggtgcc   360
tcagtcgtgt gcttcttgaa caacttctac cccaaagaca tcaatgtcaa gtggaagatt   420
gatggcagtg aacgacaaaa tggcgtcctg aacagttgga ctgatcagga cagcaaagac   480
agcacctaca gcatgagcag caccctcacg ttgaccaagg acgagtatga acgacataac   540
agctatacct gtgaggccac tcacaagaca tcaactcacc cat                     583
```

<210> SEQ ID NO 17
<211> LENGTH: 205
<212> TYPE: PRT
<213> ORGANISM: ARTIFICIAL SEQUENCE
<220> FEATURE:
<223> OTHER INFORMATION: Antibody Variable domain

<400> SEQUENCE: 17

```
Met Asp Ile Val Leu Thr Gln Ser Gln Lys Phe Met Ser Thr Ser Val
1               5                   10                  15

Gly Asp Arg Val Ser Val Thr Cys Lys Ala Ser Gln Asn Val Gly Thr
            20                  25                  30

Asn Val Ala Trp Tyr Gln Gln Lys Pro Gly Gln Ser Pro Gln Gly Leu
        35                  40                  45

Ile Tyr Ser Ala Ser Tyr Arg Tyr Ser Gly Val Pro Asp Arg Phe Thr
    50                  55                  60

Gly Ser Gly Ser Gly Thr Asp Phe Thr Leu Thr Ile Ser Asn Val Gln
65                  70                  75                  80

Ser Glu Asp Leu Ala Glu Tyr Phe Cys Gln Gln Tyr Asn Ser Tyr Pro
                85                  90                  95

Leu Thr Phe Gly Ala Gly Thr Lys Leu Glu Leu Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr His Pro
        195                 200                 205
```

<210> SEQ ID NO 18
<211> LENGTH: 8
<212> TYPE: PRT
<213> ORGANISM: ARTIFICIAL SEQUENCE
<220> FEATURE:
<223> OTHER INFORMATION: Antibody CDR

<400> SEQUENCE: 18

```
Gln Asn Val Gly Thr Asn Val Ala
1               5

<210> SEQ ID NO 19
<211> LENGTH: 11
<212> TYPE: PRT
<213> ORGANISM: ARTIFICIAL SEQUENCE
<220> FEATURE:
<223> OTHER INFORMATION: Antibody CDR

<400> SEQUENCE: 19

Gly Leu Ile Tyr Ser Ala Ser Tyr Arg Tyr Ser
1               5                   10

<210> SEQ ID NO 20
<211> LENGTH: 8
<212> TYPE: PRT
<213> ORGANISM: ARTIFICIAL SEQUENCE
<220> FEATURE:
<223> OTHER INFORMATION: Antibody CDR

<400> SEQUENCE: 20

Gln Gln Tyr Asn Ser Tyr Pro Leu
1               5
```

ANTI-FOLLISTATIN-LIKE 3 ANTIBODIES AND TREATMENT OF DIABETES

RELATED APPLICATIONS

This application is the U.S. National Stage of International Application No. PCT/US2017/055214, filed on Oct. 4, 2017, published in English, which claims the benefit of U.S. Provisional Application No. 62/404,169, filed Oct. 4, 2016. The entire teachings of the above applications are incorporated herein by reference.

GOVERNMENT SUPPORT

This invention was made with government support under Grant No. 143DK107018 awarded by the National Institutes of Health (NIH). The government has certain rights in the invention.

INCORPORATION BY REFERENCE OF MATERIAL IN ASCII TEXT FILE

This application incorporates by reference the Sequence Listing contained in the following ASCII text file:
a) File name: 51551000002_Sequence_Listing.txt; created Dec. 12, 2019, 15 KB in size.

BACKGROUND OF THE INVENTION

Diabetes affects over 30 million Americans, who consume $245 billion health care dollars to treat the disease and its long term pathologic effects. Pancreatic islets contain five different hormone-secreting cell types, including β-cells that secrete insulin and α-cells that secrete glucagon, hormones that are critical regulators of serum glucose. Since β-cells are destroyed by autoimmune attack in type 1 diabetes (T1D) (Meier, J. J. et al, Diabetalogia 48:2221-28, 2005), multiple daily insulin injections are the primary treatment for these patients. Type 2 diabetes (T2D) is caused by a combination of insufficient insulin production by remaining β-cells and reduced effectiveness of circulating insulin (Butler, A. E. et al, Diabetes 52:102-110, 2003). These patients have a number of possible treatments that focus mainly on increasing insulin production or increasing its effectiveness to address diabetes symptoms. Over time, however, T2D progresses to the point where only insulin injections can sufficiently control glucose. A recently reported in vitro procedure for differentiating human induced pluripotent stem cells (iPSCs) into functional β-cells (Pagliuca, F. W. et al, Cell 159:428-39, 2014) raises the potential that lost β-cells could ultimately be replaced by implanting iPSC-derived β-cells which could effectively cure both T1D and T2D. However, a number of technical hurdles remain to be surmounted, including large scale production of uniform functional β-cells along with encapsulation materials to prevent attack from the recipient's immune system. An alternative source to replace lost β-cells could consist of turning closely-related pancreatic cells, such as α-cells, into β-cells in a process known as transdifferentiation that has been recently demonstrated to occur in both mouse and human pancreatic tissues (Ben-Othman et al, Cell 168:1-13, 2017; Thorel, F. et al., Nature 464: 1149-1154, 2010).

Currently available treatment options for diabetes have limited efficacy, particularly as the disease progresses. Moreover, most therapies address symptoms of the disease and not the underlying cause, which is loss of insulin from beta cells. Accordingly, there exists an urgent need for new, more effective therapies for diabetes.

SUMMARY OF THE INVENTION

The present invention generally provides antibodies that bind to and inhibit one or more activities of Follistatin-like-3 (FSTL3) protein, as well as compositions comprising such antibodies, and methods of making and using such antibodies (e.g., in the treatment of diabetes).

In some embodiments, the invention provides an isolated antibody, or an antigen-binding fragment thereof, that binds to a human follistatin-like 3 (FSTL3) protein and neutralizes binding of FSTL3 to an FSTL3 ligand (e.g., Activin). In particular embodiments, the antibody, or antigen-binding fragment thereof, has one or more activities on pancreatic islet cells selected from the group consisting of increasing insulin secretion from beta cells, increasing beta cell regeneration, promoting transdifferentiation of an alpha cell or any other pancreatic cell to a beta cell, and inhibiting transdifferentiation of a beta cell to an alpha cell, or any combination thereof.

As disclosed herein, the antibodies of the invention are useful as therapeutic agents (e.g., in the treatment of diabetes). Accordingly, in other embodiments, the invention provides a method of treating diabetes in a subject in need thereof, comprising administering to the subject an effective amount of an antibody, or an antigen-binding fragment thereof, that binds to a human follistatin-like 3 (FSTL3) protein.

The present invention also provides, in some embodiments, a method of increasing insulin secretion from an islet cell (e.g., beta cell). The method comprises contacting a beta cell or other islet cell (e.g., delta cell, ghrelin cell) with an effective amount of an antibody, or an antigen-binding fragment thereof, that binds to a human follistatin-like 3 (FSTL3) protein, wherein the antibody inhibits binding of FSTL3 to an FSTL3 ligand to thereby increase insulin secretion.

In other embodiments, the present invention also provides a method of increasing beta cell regeneration. The method comprises contacting a beta cell or other islet cell (e.g., delta cell, ghrelin cell) or other activin-producing cell within or surrounding an islet (e.g., acinar cell, vascular cell, macrophage, blood cell, fibroblast) with an effective amount of an antibody, or an antigen-binding fragment thereof, that binds to a human follistatin-like 3 (FSTL3) protein, wherein the antibody inhibits binding of FSTL3 to an FSTL3 ligand to thereby enhance beta cell regeneration.

The present invention also provides, in further embodiments, a method of promoting transdifferentiation of an alpha cell or other pancreatic cell to a beta cell. The method comprises contacting an alpha cell or other pancreatic cell with an effective amount of an antibody, or an antigen-binding fragment thereof, that binds to a human follistatin-like 3 (FSTL3) protein, wherein the antibody inhibits binding of FSTL3 to an FSTL3 ligand.

In additional embodiments, the present invention also provides a method of inhibiting transdifferentiation of a beta cell to an alpha cell or other islet cell (e.g., delta cell, ghrelin cell). In an embodiment, the method is for inhibiting transdifferentiation of a beta cell to an alpha cell. The method comprises contacting a beta cell or other islet cell (e.g., delta cell, ghrelin cell) or other activin-producing cell within or surrounding an islet (e.g., acinar cell, vascular cell, macrophage, blood cell, fibroblast) with an effective amount of an antibody, or an antigen-binding fragment thereof, that binds to a human follistatin-like 3 (FSTL3) protein, wherein the antibody inhibits binding of FSTL3 to an FSTL3 ligand.

The antibodies described herein provide specific and/or enhanced inhibition of FSTL3 protein with minimal cross-reactivity to the closely related Follistatin (FST) protein. The use of such antibodies confers certain advantages, including the ability to modulate glucose metabolism in vivo with reduced potential for unwanted or harmful effects.

BRIEF DESCRIPTION OF THE DRAWINGS

The invention can be more completely understood with reference to the following drawings.

FIG. 4 shows the variation in neutralization effect of FSTL3 on different TGFβ family ligands. Doses of ligand resulting in about 100,000 light units in the neutralization assay were tested with increasing amounts of FSTL3, showing that activin A (solid circle) is neutralized by the smallest amount of FSTL3, followed by GDF11 (solid inverted triangle), activin B (solid triangle), with MSTN (solid square) exhibiting the least inhibition by FSTL3. This reflects the affinity with which FSTL3 binds each ligand but shows that FSTL3 can neutralize all four ligands.

FIGS. 5A-5D show the neutralization effect of three anti-FSTL3 antibodies on TGFβ family ligands. FP-101, FP-102, and FP-103 antibodies and a control antibody were tested for their neutralization effect on pre-determined doses of activin A (FIG. 5A), activin B (FIG. 5B), GDF11 (FIG. 5C) and myostatin (FIG. 5D). The figures show that FP-101 and FP-102 neutralize FSTL3 binding and neutralization of all four ligands while FP-103 is most effective in neutralizing FSTL3 binding and neutralization of myostatin. The control antibody had no neutralization activity.

FIGS. 6A-6C show the binding of three anti-FSTL3 antibodies to human or mouse FSTL3 proteins. Direct binding was evaluated using a Western blot. FP-101 recognized both reduced and non-reduced hFSTL3 but binding to mFSTL3 was just barely detectable (FIG. 6A). FP-102 recognized both reduced and non-reduced hFSTL3 and also recognized mouse FSTL3 better than FP-101, but to a much lower degree than it binds to human FSTL3 (FIG. 6B). FP-103 recognized both reduced and non-reduced hFSTL3 but does not recognize mFSTL3 (FIG. 6C).

FIG. 11A: After 1-2 hours, the wells were washed and an enzyme-labeled anti-mouse antibody was added that binds to the mAb in the well. mAb was detected in all samples and the value didn't change suggesting fast absorption but slow clearance so that infrequent dosing of mAb can be effective in treating diabetes. FIG. 11B: Again slow clearance of mAb was observed with detected mAb not changing significantly over 3 hours.

DETAILED DESCRIPTION OF THE INVENTION

Figure 1A:
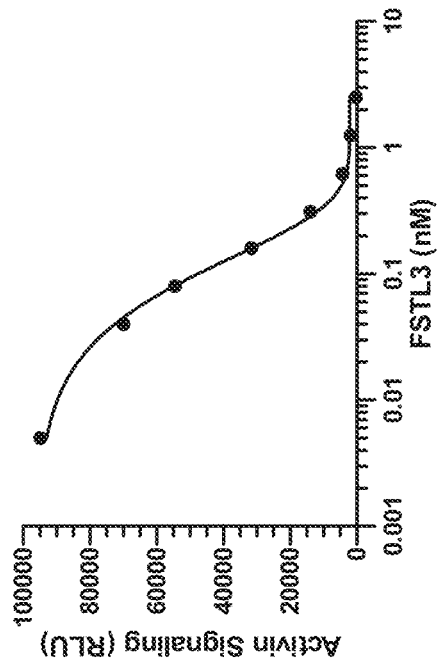
FIGS. 1A and 1B show the characteristics of a FSTL3 neutralization assay. As activin's concentration increases, signaling in the assay also increases in direct proportion. The optimal dosage of activin A required for the neutralization assay was determined as the amount of activin A that produces a stimulation of 100,000 RLU of the CAGA-Luc reporter, stably expressed in HEK 293 cells (FIG. 1A). The ability of FSTL3 to neutralize activin's activity is shown as a decrease in signaling in the assay as FSTL3 concentration increases (FIG. 1B). The optimal amount of human FSTL3 to detect inhibitors of this neutralization was determined as the amount of human FSTL3 that inhibits 90-95% of activin signaling (FIG. 1B).

A description of example embodiments of the invention follows.

Members of the TGF-beta superfamily, including activins (activin A & B), myostatin (MSTN; also known as GDF8) and growth and differentiation factor 11 (GDF11), regulate a variety of important biological processes, including lipid and glucose metabolism, both during embryogenesis and in adult tissues. Follistatin (FST) and FST-like-3 (FSTL3) proteins are secreted glycoproteins that bind and neutralize several TGF-beta superfamily proteins including activins, GDF11, and GDF8.

The antibodies against human FSTL3 (hFSTL3), or anti-hFSTL3 antibodies, disclosed herein are based on the antigen binding sites of certain monoclonal antibodies selected on the basis of binding to hFSTL3 protein (UniProt #O95633). The antibodies contain immunoglobulin variable regions with complementarity-determining region (CDR) sequences that define the antigen binding sites for the anti-hFSTL3 antibodies on the hFSTL3 protein.

The antibodies described herein have FSTL3 neutralizing activity, that is they bind to FSTL3 and prevent FSTL3 from binding to and/or neutralizing a subset of the TGFβ family of growth factors, including activin A and B, myostatin (MSTN; also referred to as GDF8) and growth and differentiation factor 11 (GDF11), and, therefore, are useful for treating various types of metabolic diseases and insulin-related disorders including Type I and II diabetes. In some embodiments (e.g., when used as therapeutic agents), the antibodies can be engineered to minimize or eliminate an immune response to the antibody when administered to a human patient. Various features and aspects of the invention are discussed in more detail below.

As used herein, "isolated antibody" means an antibody that is substantially free of its natural environment. For instance, an isolated antibody or nucleic acid is substantially free of cellular material and other proteins from the cell or tissue source from which it is derived.

As used herein, unless otherwise indicated, "antibody" means an intact antibody or antigen-binding fragment of an antibody, including an intact antibody or antigen-binding fragment that has been modified or engineered, or that is a human antibody. Examples of antibodies that have been modified or engineered are chimeric antibodies, humanized antibodies, multiparatopic antibodies (e.g., biparatopic antibodies), and multispecific antibodies (e.g., bispecific antibodies). Examples of antigen-binding fragments include Fab, Fab', F(ab')$_2$, Fv, single chain antibodies (e.g., scFv), double-stranded Fv (dsFv), minibodies and diabodies.

The antibodies disclosed herein can be whole antibodies or antibody fragments (e.g., a single-chain Fv fragment or Fab antibody fragment), provided that the antibody or antibody fragment is able to recognize and bind to its specific antigen (e.g., hFSTL3 protein) in vitro or in vivo. Such antibodies may inhibit (e.g., reduce, block, interfere with) one or more hFSTL3 activities (e.g., binding of hFSTL3 to one or more of its ligands), thereby leading to target neutralization.

The whole antibodies disclosed herein generally comprise four chains arranged in a classic "Y" motif. There are two heavy chains covalently bound to each other, and two light chains, each covalently bound to one of the heavy chains. The bottom "leg" of the "Y" is called the Fc region. The two "arms" at the top of the "Y" are called Fab regions. The Fc and the Fab regions are covalently attached. Each Fab region contains a constant region and a variable region (which extends to the tip of the "Y"). Each variable region contains antigen-binding sites (at regions within the variable regions called "hypervariable" regions) at each tip of the "Y". Thus, each Fab region has at least one antigen-binding site, and the whole antibody molecule, therefore, has two antigen-binding sites (i.e., is "bivalent").

The antibodies disclosed herein comprise: (a) an immunoglobulin heavy chain variable region comprising the structure $CDR_{H1}$-$CDR_{H2}$-$CDR_{H3}$, and (b) an immunoglobulin light chain variable region comprising the structure $CDR_{L1}$-$CDR_{L2}$-$CDR_{L3}$, wherein the heavy chain variable region and the light chain variable region together define a single binding site for binding FSTL3 protein.

Exemplary antibodies of the invention include, but are not limited to, the FP-101 and FP-102 antibodies described herein (see, e.g., FIGS. 8-11). Antibodies of the invention include, for example, antibodies having one or more (e.g., 1, 2, 3, 4, 5, or 6) heavy chain complementarity determining regions (CDRs), and/or one or more (e.g., 1, 2, 3, 4, 5, or 6) light chain CDRs of the FP-101 and/or FP-102 antibodies. Thus, in an embodiment, the invention provides an antibody, or antigen-binding fragment, comprising an antibody heavy chain variable ($V_H$) domain having at least one (e.g., 1, 2, 3, 4, 5, or 6) CDR selected from the group consisting of: a) a CDR1 consisting of SEQ ID NO:3; b) a CDR1 consisting of SEQ ID NO:13; c) a CDR2 consisting of SEQ ID NO:4; d) a CDR2 consisting of SEQ ID NO:14; e) a CDR3 consisting of SEQ ID NO:5; and f) a CDR3 consisting of SEQ ID NO:15. In particular embodiments, the antibody, or antigen-binding fragment, has all three heavy chain CDRs of the FP-101 antibody (SEQ ID NO:3; SEQ ID NO:4; and SEQ ID NO:5), or all three heavy chain CDRs of the FP-102 antibody (SEQ ID NO:13; SEQ ID NO:14; and SEQ ID NO:15).

In some embodiments, the antibody, or antigen-binding fragment, comprises an antibody variable light chain ($V_L$) domain having at least one CDR of the FP-101 and/or FP-102 antibodies. Thus, in an embodiment, the invention provides an antibody, or antigen-binding fragment, comprising an antibody light chain variable ($V_L$) domain having at least one (e.g., 1, 2, 3, 4, 5, or 6) CDR selected from the group consisting of: a CDR1 consisting of SEQ ID NO:8; a CDR1 consisting of SEQ ID NO:18; a CDR2 consisting of SEQ ID NO:9; a CDR2 consisting of SEQ ID NO:19; a CDR3 consisting of SEQ ID NO:10; and a CDR3 consisting of SEQ ID NO:20. In particular embodiments, the antibody, or antigen-binding fragment, has all three light chain CDRs of the FP-101 antibody (SEQ ID NO:8; SEQ ID NO:9; and SEQ ID NO:10), or all three light chain CDRs of the FP-102 antibody (SEQ ID NO:18; SEQ ID NO:19; and SEQ ID NO:20).

In certain embodiments, an antibody of the invention comprises all three VH CDRs (SEQ ID NO:3; SEQ ID NO:4; and SEQ ID NO:5) and all three VL CDRs (SEQ ID NO:8; SEQ ID NO:9; and SEQ ID NO:10) of the FP-101 antibody. In other embodiments, an antibody of the invention comprises all three VH CDRs (SEQ ID NO:13; SEQ ID NO:14; and SEQ ID NO:15) and all three VL CDRs (SEQ ID NO:18; SEQ ID NO:19; and SEQ ID NO:20) of the FP-102 antibody. In yet other embodiments, an antibody of the invention comprises all three VH CDRs (SEQ ID NO:3; SEQ ID NO:4; and SEQ ID NO:5) of the FP-101 antibody and all three VL CDRs (SEQ ID NO:18; SEQ ID NO:19; and SEQ ID NO:20) of the FP-102 antibody. In an additional embodiment, an antibody of the invention comprises all three VH CDRs (SEQ ID NO:13; SEQ ID NO:14; and SEQ ID NO:15) of the FP-102 antibody and all three VL CDRs (SEQ ID NO:8; SEQ ID NO:9; and SEQ ID NO:10) of the FP-101 antibody.

A person of ordinary skill in the art would recognize that, in some instances, it may be possible to combine one or more CDRs from the FP-101 antibody with one or more CDRs from the FP-102 antibody (either on the same chain or different chains) to produce an antibody that retains binding (e.g., specific binding) to FSTL3. Accordingly, the invention encompasses antibodies having CDRs from both the FP-101 and FP-102 antibodies, in any combination (e.g., a heavy chain comprising VH CDR1 and 3 from FP-101 and the VH CDR2 from FP-102).

In some embodiments, an antibody of the invention comprises the heavy chain variable region (HCVR) from the FP-101 antibody (SEQ ID NO:2), the heavy chain variable region (HCVR) from the FP-102 antibody (SEQ ID NO:12), or both. In other embodiments, an antibody of the invention comprises the light chain variable region (HCVR) from the FP-101 antibody (SEQ ID NO:7), the light chain variable region (LCVR) from the FP-102 antibody (SEQ ID NO:17), or both. Thus, possible HCVR/LCVR combinations for an antibody of the invention include SEQ ID NO:2/SEQ ID NO:12; SEQ ID NO:2/SEQ ID NO:17; SEQ ID NO:7/SEQ ID NO:12; and SEQ ID NO:7/SEQ ID NO:17. Additional functional HCVR/LCVR pairings are within the scope of the invention.

As used herein, an "antibody that binds to FSTL3, comprising" a HCVR or LCVR, means an antibody comprising the HCVR or LCVR, as opposed to a FSTL3 protein comprising the HCVR or LCVR.

In some embodiments, the antibody binds specifically to a mammalian FSTL3 (e.g., human FSTL3, or hFSTL3). This means that the antibody binds to FSTL3 protein in a sample, with negligible binding to other proteins present in the sample; under a given set of binding reaction conditions.

In some embodiments, the antibody binds specifically to FSTL3 but does not bind to Follistatin (FST) (e.g., human Follistatin (hFST)). This means that the antibody binds to FSTL3 protein in a sample, with negligible binding to FST present in the sample; under a given set of binding reaction conditions.

Examples of antigen-binding fragments of an antibody include, a Fab, Fab', F(ab')$_2$, Fv, scFv, dsFv, dAb, and a diabody.

A "Fab fragment" comprises one light chain and the CH1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab)$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

A "single-chain Fv antibody" (or "scFv antibody") refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) *The Pharmacology Of Monoclonal Antibodies*, vol. 113, Rosenburg and Moore eds. Springer-Verlag, New York, pp. 269-315. See also, PCT Publication No. WO 88/01649 and U.S. Pat. Nos. 4,946,778 and 5,260,203.

A dsFv fragment consists of a Fab fragment minus the constant regions, i.e., consisting only of the variable regions of a heavy and light chain covalently bound to each other. For a review of dsFv, see Pluckthun (1994) *The Pharmacology Of Monoclonal Antibodies*, vol. 113, Rosenburg and Moore eds. Springer-Verlag, New York, pp. 269-315.

Classically, both dsFv and scFv fragments are monovalent (and thus mono-specific). However, two dsFv fragments or two scFv fragments can themselves be linked to form a bispecific fragment (which would be analogous to an F(ab')2 fragment without the constant regions). Furthermore, it is possible to link two dsFv fragments or scFv fragments with different antigen-binding sites (i.e., different specificities), to form a bi-specific fragment.

A "diabody" is a small antibody fragment with two antigen-binding sites. The fragments comprise a heavy chain variable region (VH) connected to a light chain variable region (VL) in the same polypeptide chain (VH-VL or VL-VH). By using a linker that is too short to allow pairing between the two domains on the same chain, the domains are forced to pair with the complementary domains of another chain and create two antigen-binding sites. Diabodies are described in, e.g., patent documents EP 404,097; WO 93/11161; and Holliger et al. (1993) *Proc. Natl. Acad. Sci. USA* 90: 6444-6448.

A "domain antibody fragment" is an immunologically functional immunoglobulin fragment containing only the variable region of a heavy chain or the variable region of a light chain. In some instances, two or more VH regions are covalently joined with a peptide linker to create a bivalent domain antibody fragment. The two VH regions of a bivalent domain antibody fragment may target the same or different antigens.

In some embodiments, the antibody is modified or engineered. Examples of modified or engineered antibodies include chimeric antibodies, multiparatopic antibodies (e.g., biparatopic antibodies), and multispecific antibodies (e.g., bispecific antibodies).

As used herein, "multiparatopic antibody" means an antibody that comprises at least two single domain antibodies, in which at least one single domain antibody is directed against a first antigenic determinant on an antigen and at least one other single domain antibody is directed against a second antigenic determinant on the same antigen, Thus, for example, a "biparatopic" antibody comprises at least one single domain antibody directed against a first antigenic determinant on an antigen and at least one further single domain antibody directed against a second antigenic determinant on the same antigen.

As used herein, "multispecific antibody" means an antibody that comprises at least two single domain antibodies, in which at least one single domain antibody is directed against a first antigen and at least one other single domain antibody is directed against a second antigen (different from the first antigen). Thus, for example, a "bispecific" antibody is one that comprises at least one single domain antibody directed against a first antigen and at least one further single domain antibody directed against a second antigen, different from the first antigen.

In some embodiments, the antibodies disclosed herein are monoclonal antibodies, e.g., murine monoclonal antibodies. Methods of producing monoclonal antibodies are known in the art. See, for example, Pluckthun (1994) *The Pharmacology Of Monoclonal Antibodies*, Vol. 113, Rosenburg and Moore eds. Springer-Verlag, New York, pp. 269-315.

In some embodiments, antibodies are modified to reduce immunogenicity. When the antibodies are to be administered to a human, the antibodies can be "humanized" to reduce or eliminate antigenicity in humans. Accordingly, in some embodiments, the antibody comprises a humanized or human framework region (FR).

Methods for reducing or eliminating the antigenicity of antibodies and antibody fragments are known in the art. In one approach, a nucleic acid sequence encoding an anti-hFSTL3 antibody disclosed herein is modified, for example, by replacing the mouse constant region with human heavy- and light-chain constant regions (e.g., U.S. Pat. No. 4,816, 567; Morrison, et al., 1984, *Proc. Natl. Acad. Sci. USA*, 81:6851) to produce what is commonly referred to as a chimeric antibody.

A humanized antibody generally has one or more amino acid residues from a source that is non-human. The non-human amino acid residues are often referred to as "import" residues, and are typically taken from an "import" variable domain. Humanization can be performed generally following the method of Winter and co-workers (Jones et al., 1986, *Nature* 321:522-525; Riechmann et al., 1988, *Nature*, 332: 323-327; Verhoeyen et al., 1988, *Science* 239:1534-1536), by substituting non-human CDRs or CDR sequences for the corresponding sequences of a human antibody. In practice, humanized antibodies are typically human antibodies in which some CDR residues and possibly some FR residues are substituted by residues from analogous sites in non-human, for example, murine antibodies. Preferably, a humanized antibody has the same or substantially the same affinity and/or specificity for the antigen as the non-human, e.g., mouse antibody from which it was derived.

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-hFSTL3 antibodies are grafted into human FRs or consensus human FRs. To create consensus human FRs, FRs from several human heavy chain or light chain amino acid sequences are aligned to identify a consensus amino acid sequence. CDR grafting is described in, e.g., U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) *Nature* 321: 522-525; Riechmann et al. (1988) *Nature* 332: 323-327; Verhoeyen et al. (1988) *Science* 239: 1534-1536; and Winter (1998) *FEBS Lett* 430: 92-94.

The choice of human variable domains, both light and heavy, to be used in making the humanized antibodies is important to reduce antigenicity. According to the so-called "best-fit" method, the sequence of the variable domain of a rodent antibody is screened against the entire library of known human variable-domain sequences. The human sequence that is closest to that of the murine is then accepted as the FR for the humanized antibody (Sims et al., 1987, *J. Immunol.* 151:2296; Chothia et al., 1987, *J. Mol. Biol.* 196:901). Another method uses a particular framework derived from the consensus sequence of all human antibodies of a particular subgroup of light or heavy chains. The same framework may be used for several different humanized antibodies (Carter et al., 1992, *Proc. Natl. Acad. Sci. USA* 89:4285; Presta et al., 1993, *J. Immunol.* 151:2623).

It is important for humanized antibodies to retain affinity for the antigen and other desirable biological properties (e.g., including specificity and/or neutralization activity). To achieve this result, humanized antibodies can be designed analyzing parental sequences and various conceptual humanized products using three-dimensional models of the parental and humanized sequences. Three-dimensional immunoglobulin models are commonly available and are familiar to those skilled in the art. Computer programs that illustrate and display probable three-dimensional conformational structures of selected candidate immunoglobulin sequences are available. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Other methods to reduce immunogenicity include "reshaping," "hyperchimerization," and "veneering/resurfacing." See, e.g., Vaswami et al., 1998, *Ann. Allergy & Immunol.* 81:105; Roguska et al., 1996, *Prot. Engineer.* 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ antibody discovery platform (Vaccinex, Inc., Rochester, N.Y.), which involves use of a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ antibody engineering platform, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Humanization of antibodies is routine protein engineering. Nearly all murine antibodies can be humanized by CDR grafting, resulting in the retention of antigen binding. See, e.g., Lo, Benny, K. C., editor, in *Antibody Engineering: Methods and Protocols*, Vol. 248, Humana Press, New Jersey, 2004.

In some embodiments, the antibodies or antigen binding fragments are antagonists. As used herein, "antagonist" in reference to an anti-hFSTL3 antibody means an antibody that inhibits the binding to and/or neutralization of the TGF-beta family of ligands, including activins (activin A&B), myostatin and GDF11, by FSTL3 protein. An antagonist anti-hFSTL3 antibody may inhibit one or more activities of the human FSTL3 protein selected from the group consisting of: FSTL3 binding to activin A, FSTL3 binding to activin B, FSTL3 binding to myostatin, FSTL3 binding to growth differentiation factor 11 (GDF11), inhibition of activin A signaling, inhibition of activin B signaling, inhibition of myostatin signaling, and inhibition of GDF11 signaling, or a combination thereof.

In some embodiments, the antibodies or antigen binding fragments are "neutralizing" antibodies or antigen-binding fragments. As used herein, a "neutralizing antibody or antigen-binding fragment" refers to an antibody or antigen-binding fragment that, upon binding to FSTL3, inhibits (e.g., blocks, prevents) binding of any one or more of the TGF-beta family of ligands (e.g., activins (activins A & B), myostatin and GDF11) to FSTL3, and/or releases ligand that is already bound to FSTL3. In both cases, an effect of binding of the neutralizing antibody to FSTL3 is to increase free ligand to stimulate its downstream signaling and activity. Neutralizing activity of an antibody of the invention can be assessed, for example, using the CAGA-luc assay disclosed herein.

Figure 1B:
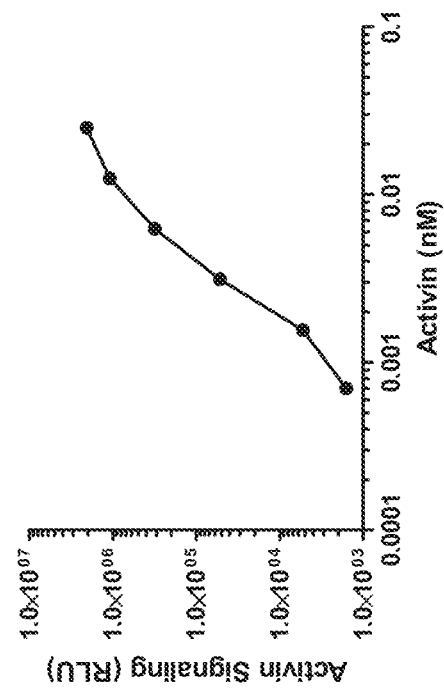
Figure 3:
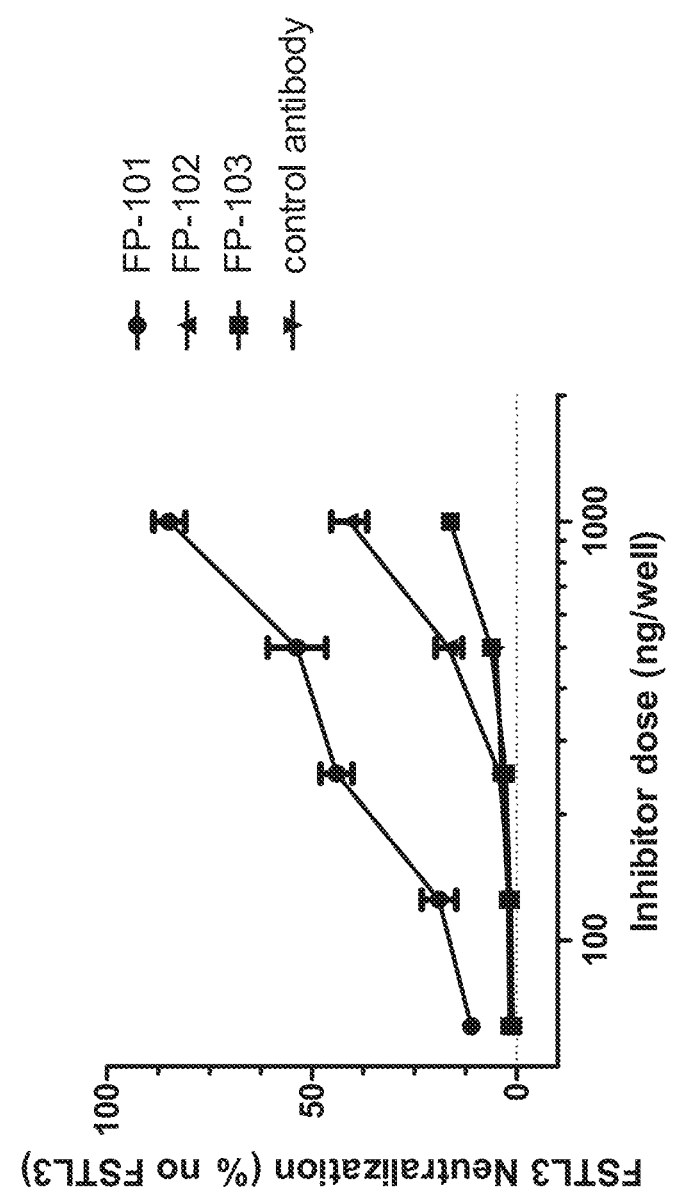
FIG. 3 shows the results of the cell-based neutralization assay using purified antibodies against human FSTL3 (hFSTL3). Three anti-hFSTL3 antibodies and a control antibody were evaluated for their neutralization activity. Neutralization activity was monitored by the ability of the test antibody to neutralize FSTL3 binding to activin, which increases the amount of free activin which stimulates light produced by the CAGA-Luc reporter. Antibody FP-101 showed the highest neutralization activity, followed by the FP-102 and the FP-103 antibodies. The control antibody, which bound to, but did not neutralize FSTL3, had no activity in this assay.

In some embodiments, a "neutralizing antibody or antigen-binding fragment" can inhibit binding of FSTL3 to one or more of its ligands by greater than about 50% (a greater than 50% reduction in ligand binding), such as about 60%, 70%, 80%, 90%, 95%, 98%, 99% or 100% inhibition, compared to a control (e.g., no antibody present). Percentage inhibition can be measured by the ability of the inhibitor (e.g., anti-hFSTL3 antibody) to inhibit one or more activities of the human FSTL3 protein selected from the group consisting of: FSTL3 binding to activin A, FSTL3 binding to activin B, FSTL3 binding to myostatin, FSTL3 binding to growth differentiation factor 11 (GDF11), inhibition of activin A signaling, inhibition of activin B signaling, inhibition of myostatin signaling, and inhibition of GDF11 signaling, or a combination thereof, as shown in FIGS. 1B and 3 for activin stimulation of CAGA-Luc activity. Percent inhibition is not a fixed characteristic, but depends on the affinity of the antibody for FSTL3 and their relative concentrations. In general, the more antibody present relative to FSTL3, the greater will be the percent neutralized, assuming the antibody has any neutralizing activity.

Methods for determining whether a test antibody (e.g., antibody described herein) binds to a target antigen are known in the art. For example, Western blot, Solid-phase ELISA, and/or conventional ELISA assays can be used to determine whether the test antibody binds to the target antigen. Methods for antibody characterization, including determination of binding specificity, affinity, functional activity and biological activity, are well known in the art. For example, the "neutralization assay" described in the Example section herein can be used to determine the functional activity (e.g., inhibition of binding to and/or neutralization of TGF-beta family of ligands by FSTL3) of the test antibody.

An antibody that binds to FSTL3 and competitively inhibits the binding of an antibody of the invention disclosed herein (e.g., FP-101, or FP-102) is also within the scope of the invention. Methods for determining whether two or more antibodies compete for binding to the same target are known in the art. For example, a competitive binding, or competition, assay can be used to determine whether one antibody blocks the binding of another antibody to the target. Typically, a competition assay involves the use of purified target antigen (e.g., FSTL3) bound to a solid substrate or expressed on cells, an unlabeled test binding molecule (e.g., a test anti-hFSTL3 antibody), and a labeled reference binding molecule (e.g., an antibody disclosed herein). Competitive inhibition is measured by determining the amount of label bound to the solid substrate or cells in the presence of the test molecule. Usually (but not necessarily) the molecule is present in excess of at least two-fold. A test antibody competes with the reference antibody for specific binding to the antigen if an excess of one antibody inhibits binding of the other antibody by at least 50%, as measured in a competition assay.

The present invention provides isolated nucleic acids comprising a nucleotide sequence encoding an antibody or a fragment (e.g., a HCVR and/or a LCVR disclosed herein, or a fragment thereof). A nucleic acid according to the present invention may comprise DNA or RNA, and may be wholly or partially synthetic. For example, DNA molecules encoding an HCVR and/or LCVR disclosed herein can be chemically synthesized. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, nucleotide sequences can be cloned out of hybridomas, for example, by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Techniques and protocols for engineering and production of nucleic acids are known in the art. See, e.g., *Current Protocols in Molecular Biology*, Second Edition, Ausubel et al. eds., John Wiley & Sons, 1992.

A nucleotide sequence encoding an antibody of the invention can be operably linked to a promoter to effect expression of the antibody in a host cell. The sequence may include at its 5' end a leader sequence to facilitate expression in a host cell and/or secretion of the antibody from a host cell. Suitable leader sequences are known in the art and can be selected by the skilled person, taking account of the host cell.

In some embodiments, the nucleic acid is incorporated into a vector. Suitable vectors containing appropriate regulatory sequences, including promoter sequences, terminator sequences, polyadenylation sequences, enhancer sequences, marker genes and other sequences as appropriate, can be obtained commercially or constructed by persons of skill in the art. For further details see, e.g., *Molecular Cloning: a Laboratory Manual*, 2nd edition, Sambrook et al., 1989, Cold Spring Harbor Laboratory Press. Examples of vectors include plasmids, phages, phagemids, and cosmids, as well as transcription and expression cassettes.

Nucleic acids encoding a HCVR and/or a LCVR disclosed herein can be incorporated (ligated) into expression vectors, which can be introduced into host cells through conventional transfection or transformation techniques. Accordingly, a host cell can be transformed with an expression vector comprising a nucleotide sequence encoding a HCVR and/or a LCVR, or a fragment thereof. Examples of host cells include *E. coli* cells, Chinese hamster ovary (CHO) cells, human embryonic kidney 293 (HEK 293) cells, HeLa cells, baby hamster kidney (BHK) cells, monkey kidney cells (COS), and human hepatocellular carcinoma cells (e.g., Hep G2).

Methods of producing an antibody or a fragment (e.g., a HCVR and/or a LCVR disclosed herein, or a fragment thereof) are within the scope of the invention. In some embodiments, the method comprises: (a) growing a host cell containing an expression vector encoding the HCVR and/or LCVR under conditions so that the host cell expresses the antibody comprising the HCVR and/or LCVR, or a fragment thereof; and (b) isolating the antibody comprising the HCVR and/or LCVR, or a fragment thereof.

Suitable conditions for antibody expression and isolation or purification depend on the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO (Chinese hamster ovary) cells, it is first inserted into an expression vector containing a suitable eukaryotic promoter, a secretion signal, a poly A sequence, and a stop codon. Optionally, the vector or gene construct contains enhancers and introns. This expression vector optionally contains sequences encoding all or part of a constant region, enabling an entire, or a part of, a heavy or light chain to be expressed. The gene construct can be introduced into eukaryotic host cells using conventional techniques. The host cells express VL or VH fragments, VL-VH heterodimers, VH-VL or VL-VH single chain polypeptides, complete heavy or light immunoglobulin chains, or portions thereof, each of which may be attached to a moiety having another function (e.g., cytotoxicity).

In some embodiments, a host cell is transfected with a single vector expressing a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In some embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced, for example, by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as Protein A, Protein G, glutathione-S-transferase (GST), or histidine tags.

The antibodies of the present invention can be produced by growing (culturing) a hybridoma (e.g., obtained by traditional monoclonal antibody techniques) expressing the antibody. The antibodies of the present invention can also be produced by growing (culturing) a host cell transfected with, for example: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

In some embodiments, anti-hFSTL3 antibodies are linked to a different functional molecule or moiety, e.g., a peptide, protein, toxin, radioisotope, or cytostatic agent, for various purposes such as therapeutic uses. The antibodies can be linked by chemical cross-linking or by recombinant methods. The antibodies also can be linked to any of various nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their circulating half-life. Examples of polymers and methods to attach them are described in U.S. Pat. Nos. 4,766,106; 4,179,337; 4,495,285; and 4,609,546.

Formulations

In some embodiments, the antibodies or the antigen-binding fragments are formulated into compositions (e.g., pharmaceutical compositions) suitable for administration to a mammal, e.g., a human patient. The compositions typically comprise one or more antibodies of the present invention and a pharmaceutically acceptable excipient. The term "pharmaceutically acceptable excipient" includes suitable solvents, dispersion media, coatings, antibacterial agents and antifungal agents, isotonic agents, and absorption delaying agents, and the like, that are compatible with pharmaceutical administration. The use of such media and agents for pharmaceutically active substances is known in the art. The compositions also can contain other active compounds providing supplemental, additional, or enhanced therapeutic functions. In one embodiment, the composition can contain a myostatin inhibitor. The pharmaceutical compositions also can be included in a container, pack, or dispenser together with instructions for administration.

A pharmaceutical composition of the invention can be formulated to be compatible with its intended route of administration. Methods to accomplish the administration are known in the art. The administration may be parenteral or non-parenteral, including intravenous, intra-arterial, intraperitoneal, intramuscular, intracavity, subcutaneous, intradermal, topical, inhalation, transmucosal, rectal or transdermal.

Solutions or suspensions used for intradermal or subcutaneous application typically include one or more of the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose. The pH can be adjusted with acids or bases, as necessary. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. Sterilization can be accomplished, for example, by filtration through sterile filtration membranes. For intravenous administration, suitable carriers include, for example, physiological saline, bacteriostatic water, Cremophor EL (BASF, Parsippany, N.J.) or phosphate buffered saline (PBS). Preferably, the pharmaceutical composition is stable under the conditions of manufacture and storage and is preserved against contamination by microorganisms such as bacteria and fungi. Avoidance of microorganisms can be achieved by inclusion of antibacterial and/or antifungal agents. Examples include: parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. The carrier can be a solvent or dispersion medium containing, for example, water, ethanol, polyol such as glycerol, propylene glycol, liquid polyethylene glycol, and the like, and suitable mixtures thereof. The proper fluidity can be maintained, for example, by the use of a coating such as lecithin, by the maintenance of the required particle size in the case of dispersion and/or by the use of surfactants. Prolonged absorption of the injectable compositions can be achieved by including in the composition an agent that delays absorption, e.g., aluminum monostearate or gelatin.

Oral compositions generally include an inert diluent or an edible carrier. They can be enclosed in gelatin capsules or compressed into tablets. For oral administration, the antibodies can be combined with excipients and used in the form of tablets, troches, or capsules.

For transmucosal or transdermal administration, penetrants appropriate to the barrier to be permeated can be used in the formulation. Such penetrants are known in the art, and include, for example, detergents, bile salts, and fusidic acid derivatives. Transmucosal administration may be accomplished, for example, through the use of lozenges, nasal sprays, inhalers, or suppositories. For example, in case of antibodies that comprise the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated into ointments, salves, gels, or creams as generally known in the art. For administration by inhalation, the antibodies may be delivered in the form of an aerosol spray from pressured container or dispenser, which contains a suitable propellant, e.g., a gas such as carbon dioxide, or a nebulizer.

In some embodiments, the presently disclosed antibodies are formulated with carriers that protect the antibody against rapid elimination from the body, such as a controlled release formulation, including implants and microencapsulated delivery systems. Biodegradable, biocompatible polymers can be used. Exemplary polymers include ethylene vinyl acetate, polyanhydrides, polyglycolic acid, collagen, polyorthoesters, polylactic acid, and polyethylene glycol (PEG). Methods for preparation of such formulations will be apparent to those skilled in the art. Liposomal suspensions containing the presently disclosed antibodies can also be used as pharmaceutically acceptable carriers. These can be prepared according to methods known in the art. See, e.g., U.S. Pat. No. 4,522,811.

In some embodiments, pharmaceutical compositions contain, in addition to an antibody of the invention, a cytotoxic, cytostatic, anti-angiogenic agent, a tumor targeted agent, an immune stimulating or immune modulating agent, or an antibody conjugated to a cytotoxic, cytostatic, or otherwise toxic agent. In one embodiment, the pharmaceutical composition comprising the antibody, or antigen-binding fragment of the current invention further comprises a myostatin inhibitor. The pharmaceutical composition optionally can be employed with other therapeutic modalities such as surgery, chemotherapy, and radiation.

Toxicity and therapeutic efficacy of the composition of the invention can be determined by conventional pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

A therapeutically effective dose of an antibody can be estimated initially, e.g., from cell culture assays. Examples of suitable bioassays include DNA replication assays, cytokine release assays, transcription-based assays, binding assays, neutralization assays, assays based on the differentiation of pre-adipocytes, assays based on glucose uptake in adipocytes, metabolic assays other assays as, for example, described in the Examples. The data obtained from the cell culture assays and animal studies can be used in formulating a range of dosage for use in humans. A dose may be formulated in animal models to achieve a circulating plasma concentration range that includes the $IC_{50}$ (i.e., the concentration of the antibody that achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending upon the dosage form employed and the route of administration.

Generally, a therapeutically effective amount of an antibody or a composition described herein is in the range of 0.1 mg/kg to 100 mg/kg, preferably 0.1 mg/kg to 50 mg/kg. The amount administered will depend on variables such as the type and extent of disease or indication to be treated, the overall health of the patient, the in vivo potency of the antibody, the pharmaceutical formulation, the serum half-life of the antibody, the route of administration and the biodistribution of the antibody.

Administration frequency can vary, depending on factors such as route of administration, dosage amount, serum half-life of the antibody or the antigen-binding fragment thereof, and the disease being treated.

Uses of FSTL3 Antibodies of the Invention

The invention provides, in other embodiments, methods of treating metabolic diseases (e.g., diabetes) or disorders in a subject, e.g., a human patient, comprising administering an effective amount of an antibody or antigen-binding fragment of the present invention to a mammal in need thereof. In some embodiments, the method is a method of treating insulin-related disorders. As used herein, "insulin-related disorders" refers to disorders involving production, regulation, metabolism, and action of insulin in a subject. Insulin-related disorders include, but are not limited to, pre-diabetes, type 1 diabetes mellitus, type 2 diabetes mellitus, hypoglycemia, hyperglycemia, insulin resistance, secretory dysfunction, loss of pancreatic β-cell function, and loss of pancreatic ft-cells. In some embodiments, the method is a method of treating diabetes (e.g., Type I or Type II).

As used herein, "treat", "treating" or "treatment" means inhibiting or relieving a disease or disorder. For example, treatment can include a postponement of development of the symptoms associated with disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

As used herein, "subject" refers to a mammal (e.g., human, non-human primate, cow, sheep, goat, horse, swine, dog, cat, rabbit, guinea pig, rat, mouse). In a particular embodiment, the subject is a human. A "subject in need thereof" refers to a subject (e.g., patient) who has, or is at risk for developing, a disease or condition that can be treated (e.g., improved, ameliorated, prevented) by of an antibody or antigen-binding fragment of the present invention. (e.g., anti-hFSTL3 antibody). In certain embodiments, the subject is human. In some embodiments, the subject has been diagnosed with type I or II diabetes. In other embodiments, the subject is pre-diabetic. In some embodiments, the diabetic subject is a subject who has also been diagnosed with a metabolic disease or is over 55 years of age, or both. In certain embodiments, the subject is a veterinary animal diagnosed with a metabolic disease (e.g., diabetes). In some embodiments, a subject in need thereof is a subject with type 2 diabetes in need of improved glycemic control with well or poorly controlled free blood glucose (FBG) and/or postprandial blood glucose (PPG). In various aspects of the embodiment need for improved glycemic control is determined by various methods that are well known in the art including determination of HbA1c level, 1- or 2-hour PPG, or oxidative stress. In one embodiment the subject is not currently receiving any other drug treatment and the agents described herein (e.g., anti-hFSTL3 antibodies) are used as the sole pharmacologic agent. In another embodiment the subject is undergoing treatment with an oral suppressors of hepatic glucose output (e.g., metformin) and the agent described herein (e.g., anti-hFSTL3 antibody) is added to the treatment regimen.

An agent (e.g., antibody or antigen-binding fragment thereof that inhibits one or more activities of FSTL3 protein described herein (and thereby treats metabolic diseases including diabetes)) can be administered to a subject in need thereof by a variety of routes of administration that are well known in the art including, for example, oral, dietary, topical, transdermal, inhalation, transmucosal, rectal, or parenteral (e.g., intra-arterial, intravenous, intramuscular, subcutaneous injection, intradermal injection, intraperitoneal, intra-cavity) routes of administration. Administration can be local or systemic or a combination thereof. The chosen mode of administration can vary depending on the multiple factors including but not limited to the nature of the disease to be treated, subject, dosage of the agent selected and/or frequency of administration. The actual dose of the agent and treatment regimen can be determined by a skilled physician, taking into account the nature of the condition being treated, and patient characteristics.

As used herein, the term "effective amount" means an amount of an anti-hFSTL3 antibody, that when administered alone or in combination with an additional therapeutic agent to a cell, tissue, or subject, is effective to achieve the desired therapeutic or prophylactic effect under the conditions of administration. For example, an effective amount is one that would be sufficient to enhance or diminish the immune response to bring: about effectiveness of a therapy. The effectiveness of a therapy (e.g., activation activin signaling, increased insulin sensitivity in the islets, increasing insulin secretion from a cell, or regulation of glucose metabolism) can be determined by suitable methods known in the art.

In some embodiments, anti-hFSTL3 antibodies of the invention are administered with one or more additional therapeutic agents, e.g., an anti-diabetes agent (e.g., insulin), or an inhibitor (e.g., myostatin inhibitor). The antibody can be linked to the agent (as an immunocomplex) or administered separately. In some embodiments, the additional therapeutic agent is an inhibitor of TGF-beta super family of growth factors (e.g., activin or myostatin inhibitor). In separate administration, the antibody can be administered before, after or concurrently with the agent or can be co-administered with other known therapies. Combination therapies are known in the art. See, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Philadelphia, Pa.

In some embodiments, an antibody disclosed herein is used as a targeting agent for delivery of a payload, e.g., a toxin, to a cell expressing FSTL3. The method includes administering an anti-hFSTL3 antibody conjugated to a payload moiety. Suitable conjugation methods are known in the art.

The present invention also provides, in some embodiments, a method of increasing insulin secretion from an islet cell (e.g., beta cell). The method comprises contacting a beta cell or other islet cell (e.g., delta cell, ghrelin cell) with an effective amount of an antibody, or an antigen-binding fragment thereof, that binds to a human follistatin-like 3 (FSTL3) protein, wherein the antibody inhibits binding of FSTL3 to an FSTL3 ligand. Insulin secretion can be measured by directly measuring the levels of insulin secreted by these cells into culture medium, or into the circulation when inside an animal or human. Methods to measure and quantitate levels of insulin are well known in the relevant art and readily available commercially. The method can be performed in vitro, in vivo or ex vivo.

In other embodiments, the present invention also provides a method of increasing beta cell regeneration. The method comprises contacting a beta cell or other islet cell (e.g., delta cell, ghrelin cell) or other activin-producing cell within or surrounding an islet (e.g., acinar cell, vascular cell, macrophage, blood cell, fibroblast) with an effective amount of an antibody, or an antigen-binding fragment thereof, that binds to a human follistatin-like 3 (FSTL3) protein, wherein the antibody inhibits binding of FSTL3 to an FSTL3 ligand. Techniques and assays for assessing beta cell regeneration are known in the art. The method can be performed in vitro, in vivo or ex vivo.

The present invention also provides, in further embodiments, a method of promoting transdifferentiation of an alpha cell or other pancreatic cell to a beta cell. The method comprises contacting an alpha cell or other pancreatic cell with an effective amount of an antibody, or an antigen-binding fragment thereof, that binds to a human follistatin-like 3 (FSTL3) protein, wherein the antibody inhibits binding of FSTL3 to an FSTL3 ligand. Techniques and assays for assessing transdifferentiation of alpha cells to beta cells are known in the art. The method can be performed in vitro, in vivo or ex vivo.

In additional embodiments, the present invention also provides a method of inhibiting transdifferentiation of a beta cell to an alpha cell or other pancreatic cell. The method comprises contacting a beta cell with an effective amount of an antibody, or an antigen-binding fragment thereof, that binds to a human follistatin-like 3 (FSTL3) protein, wherein the antibody inhibits binding of FSTL3 to an FSTL3 ligand.

Techniques and assays for assessing transdifferentiation of a beta cells to alpha cells are known in the art. The method can be performed in vitro, in vivo Or ex vivo.

Cells expected to respond to treatment are those that make insulin, which in vivo is limited to beta cells outside the brain (e.g., pancreatic beta cells) as well as various cell lines used for in vitro studies such as Ins1, TC, RIN, MIN, etc. insulin-secreting cells described herein can be obtained from various sources using methods known in the art. Such cells can be used for various in vitro, in vivo and/or ex vivo applications. Procedures such as islet isolation (Brown et al Islets 3:367-75, 2011 and references therein) or differentiation of embryonic stem cells or induced pluripotent stem cells into functional beta cells (Pagliuca et al Cell 159:428-439 201.4) are routinely used to obtain enriched populations of beta cells used in the method described here.

EXAMPLES

The following Examples are merely illustrative, and are not intended to limit the scope or content of the invention in any way.

Materials and Reagents

Antibodies:

For western blot, primary antibodies are anti-FSTL3 monoclonals produced for Fairbanks Pharmaceuticals by Neo Scientific in Woburn Mass., including FP-101, FP-102 and FP-103. Secondary antibody (donkey anti-mouse IgG-Horse Radish Peroxidase label) was purchased from Jackson Immuno Research in West Grove Pa. Human FSTL3 was produced by Fairbanks Pharmaceuticals by cloning the human FSTL3 cDNA into an expression plasmid containing a 6-His tag. 293 cells were transfected with this plasmid and stable colonies selected. Cells were grown for 7-14 days, medium collected, and FSTL3 was purified on Nickel-Sepharose-Sephadex Beads (GE Healthcare Life Sciences, Pittsburgh Pa. Ligands: activin A (Cat No:338-AC-050), activin B (Cat No:659-AB-005), and MSTN (Cat No:788-68-010) were purchased from R&D Systems (Minneapolis, Minn.). GDF11 (Cat No:TP723130), was purchased from Origene (Rockville Md.)

Example 1. Luciferase Assay to Determine Optimal Amount of Human FSTL3 Required for the Neutralization of Activin A Luciferase reporter assays were performed with a HEK293-(CAGA) cell line that stably expresses a (CAGA)-luciferase reporter gene, which was generated as previously described in Cash et. al., (*J. Biol. Chem.* 2012, 287, 1043-1053), which is incorporated by reference in its entirety. Cells were treated with varying amounts of activin A in serum-free medium for 24 h to determine the optimal dose of activin A required for the assay. Cells were washed with DPBS between removal of growth medium and addition of activin A in test medium which was DMEM with 0.1% BSA (Sigma, St Louis). FIG. 1A shows that increasing activin A dose causes an increase in luciferase biosynthesis, which is visualized as light when dual glow solution (Promega E2910) or similar commercial product is added. Background obtained from cells with no activin A treatment was less than 1000 relative light units (RLU). The optimal dosage of activin A required for reliable detection in a neutralization assay was determined by the amount of activin A that produced a stimulation of 100,000 RLU of cells treated with activin A. This amount was determined to correspond to 0.005-0.010 nM activin A (FIG. 1A). FIG. 1B shows a linear inhibition of activin A that depends on the amount of human FSTL3 present in each well. For the neutralization assay, the amount of human FSTL3 required to inhibit 90-95% of activin A signaling was chosen as an optimal amount required for reliably detecting both the neutralizing compounds as well as non-specific interference in the assay that would further reduce the observed RLU readout. This amount was determined to correspond to 0.0625-0.123 nM of human FSTL3 (FIG. 1B). Therefore, it was determined that the screening assay described in Example 2 would consist of HEK293 cells stably expressing the CAGA-Luc reporter, 0.005 nM activin A, and 0.0625 nM human FSTL3.

Example 2. Screening of Monoclonal Antibodies and Antibody Characterization

A. Screening of Antibodies for Binding to Human FSTL3

Figure 2:
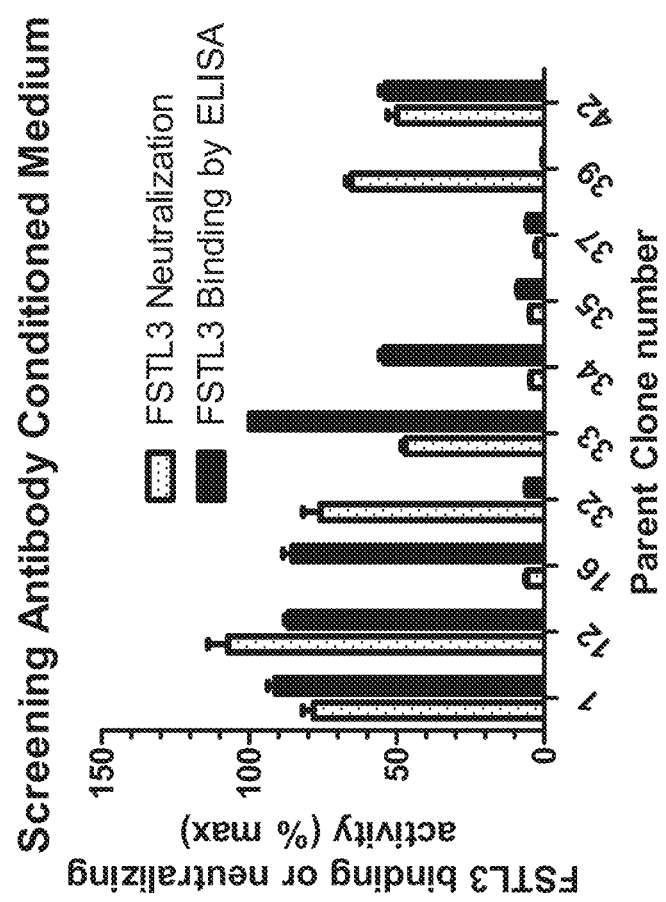
FIG. 2 is a bar graph summarizing the screening results of 10 antibodies, all of which bind to FSTL3 to some degree. Neutralization of FSTL3 activity was detectable in a subset of clones and varied widely, demonstrating the need for a screening assay to detect neutralization.

Binding of antibodies to FSTL3 was determined by incubating 250 ng hFSTL3/well in 100 μl of 0.1M Carbonate buffer pH 9 in immulon plastic 96 well plates overnight. The medium was aspirated and 200 μl of 3% BSA in phosphate buffered saline was added for 2 hours to block non-specific binding. This material was aspirated and 50 μl of conditioned medium containing anti-FSTL3 monoclonal antibodies (produced for Fairbanks Pharmaceuticals by Neo Scientific by standard monoclonal antibody methods in normal Balb-C mice) was added for 2-4 hours. Unbound protein was removed by washing three times for 5 min with 200 μl wash buffer (0.01% Tween in 10 mm PBS solution). 100 μl of secondary antibody (Goat-anti-Mouse IgG-Alkaline Phosphatase) was then placed in the wells. At the end of this step, the wells are washed again and a substrate for the enzyme was added, resulting in the production of a yellow color that is directly proportion to the amount of antibody bound. Binding of antibodies to human FSTL3 was determined and the results were plotted in a bar graph. FIG. 2 shows that while all clones recognized human FSTL3 to some extent, the amount of antibody binding to human FSTL3 varied widely among the different antibody clones. These same 10 colonies with consistent FSTL3 binding were used for assessing the neutralization activity, as described below.

B. Screening of Antibodies for Neutralization Activity Against Human FSTL3

Neutralization assay was performed as described above in Example 1. Briefly, 50 μl of the medium, from each of the 10 colonies used for the binding assay described above were added to tubes containing 0.005 nM activin A and 0.0625 nM human FSTL3, and the mixture was added to 96-well plates containing HEK293 cells stably expressing the CAGA-Luc reporter. After 16-24 hours, luminescence measurements were taken as described earlier. The "neutralizing activity" was calculated as (100−(antibody medium RLU/ Maximum RLU×100)) and the results were plotted in a bar graph (FIG. 2) alongside the binding results for each clone. FIG. 2 shows that the "neutralizing activity" of the antibodies tested varied widely, with only 6 antibodies (1, 12, 31, 33, 39, and 42) showing detectable neutralization activity. The best three subclones from these 6 parental antibodies were selected, and the antibody was purified from larger batches of conditioned medium. These clones are now referred to as clones 12 (FP-101), 33 (FP-102) and 1 (FP-103). The purified antibody from each clone was evaluated further for neutralization activity. FIG. 3 shows the combined results from 4 experiments in which increasing doses of the three antibody clones show increasing amounts of neutralization. At each dose of antibody, antibody FP-101 showed the highest neutralization activity followed by the FP-102 and the FP-103 antibodies. The control antibody, which bound to, but did not neutralize human FSTL3, had no activity in this assay.

Example 3. Neutralization Activity of Anti-hFSTL3 Antibodies on Human FSTL3 Bound to TGFβ-Family Ligands A. Neutralization of TGFβ-Family Ligands by Human FSTL3

A luciferase assay was performed as described above in Example 1. Varying amounts of human FSTL3 were mixed with varying pre-determined amounts of activin A, activin B, GDF11 or myostatin ligands (that produce approximately 100,000 RLU) in 96-well plates containing 293-Caga Luc cells. Luminescence measurements were taken as described earlier and the results were plotted (FIG. 4). FIG. 4 shows that the amount of human FSTL3 required to neutralize varied widely among the different ligands tested. The smallest amount of FSTL3 was required to neutralize activin A (solid circle) compared to the other ligands (see FIG. 4, the curve with the solid circle is shifted to left relative to the other curves). GDF11 (solid inverted triangle) and activin B (solid triangle) are neutralized by increasing amounts of FSTL3 in the order referenced herein. MSTN (solid square) exhibits the least inhibition by FSTL3. Nevertheless, these results demonstrate that FSTL3 neutralizes all four ligands, so that neutralization of FSTL3 could increase the bioactivity of any or all of these four ligands if present in a particular cell, cell medium, or physiological fluid such as blood, urine, or seminal plasma.

B. Neutralization Assay with Anti-hFSTL3 Antibodies and TGFβ-Family Ligands

A neutralization assay was performed as described above in Example 2. 1000 ng/well of test anti-hFSTL3 antibodies were mixed with wells pre-incubated with HEK293 cells stably expressing the CAGA-Luc reporter and pre-determined amounts (see inset of FIG. 4) of activin A, activin B, GDF11 or myostatin ligands and hFSTL3 (see FIG. 4) in 96-well plates. Luminescence measurements were taken as described earlier and the results were plotted in bar graphs (FIGS. 5A-5D). Results demonstrate that both FP-101 and FP-102 can completely neutralize FSTL3 bound to activin A (FIG. 5A), activin B (FIG. 5B), and GDF11 (FIG. 5C). FP-103 neutralizes only about 40% of the activity of FSTL3 bound to activin A (FIG. 5A), activin B (FIG. 5B), and GDF11 (FIG. 5C). The results of FP-101 and FP-102-induced neutralization of FSTL3 bound to myostatin (FIG. 5D) were similar to the effects of these antibodies on other tested ligands. FP-103 was also able to neutralize myostatin signaling equally well as the other antibodies. The control antibody did not show any detectable "neutralization activity" for any of the tested ligands. These results confirm that treatments neutralizing FSTL3 would lead to increased free (and therefore bioactive) activin A and B, GDF11, and myostatin.

Example 4. Binding of Anti-hFSTL3 Antibodies to Mouse and Human FSTL3 and not to Human Follistatin Direct binding studies were conducted by performing Western blot, a technique well known in the art. Pre-determined doses of human FSTL3 (hFSTL3) or mouse FSTL3 (mFSTL3), that are easily detectable at the end of experimentation, were loaded onto SDS gels (10% NuPage gels). After electrophoresis, proteins were transferred to PVDF membranes and then tested with the selected and purified anti-hFSTL3 antibodies from FIG. 3. Binding of test antibodies to human or mouse FSTL3 was determined and shown in FIGS. 6A-6C. FP-101 recognized both reduced and non-reduced hFSTL3, but binding to mFSTL3 was just barely detectable (FIG. 6A). FP-102 recognized both reduced and non-reduced hFSTL3, and also recognized mouse FSTL3 better than FP-101, but to a much lower degree than it binds to human FSTL3 (FIG. 0.6B). FP-103 recognized both reduced and non-reduced hFSTL3 but did not recognize mouse FSTL3 (FIG. 6C).

Figure 7A:
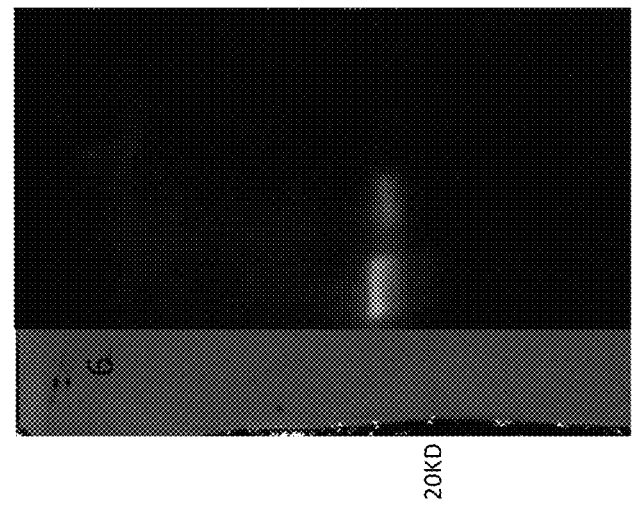
FIGS. 7A and 7B show the comparative binding of FP-101 and FP-102 antibodies to human FSTL3 and human Follistatin proteins. Direct binding was evaluated using Western blot. Both the FP-101 (FIG. 7A) and FP-102 (FIG. 7B) antibodies bind to reduced (RED) and non-reduced (NR) human FSTL3 (ASL11), but neither FP-101 (FIG. 7A) nor FP-102 (FIG. 7B) bind to reduced and non-reduced human Follistatin (hFST).
Figure 7B:
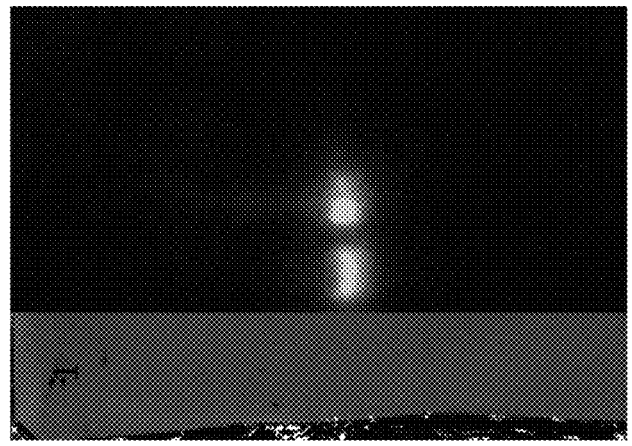

Using Western blot as described above, binding of anti-hFSTL3 test antibodies to human Follistatin (hFST) was evaluated. Pre-determined doses of hFSTL3 or hFST, that were in the same range as in the experiment described above, were loaded onto SDS gels (10% NuPage gels). FIGS. 7A-7B show the binding of the test antibodies to hFSTL3 or hFST. Both the FP-101 (FIG. 7A) and FP-102 (FIG. 7B) antibodies bind to human FSTL3, but neither FP-101 (FIG. 7A) nor FP-102 (FIG. 7B) bind to human FST. These results demonstrate that the panel of test antibodies (FP-101 and FP-102) has an advantageous property of specificity to human FSTL3 protein without cross reactivity to human Follistatin. Therefore the probability for side effects due to follistatin neutralization is reduced or eliminated.

Example 5. Identification of Complementarity-Determining Regions (CDRs) of Anti-hFSTL3 Antibodies The cells making and secreting the FP-101 anti-hFSTL3 antibody were homogenized and intact RNA was extracted. Using standard techniques that are well known in the art, intact RNA transcripts were converted to cDNA and then amplified using primers that bind to sequences found in all mouse antibodies. The resulting amplified DNA was sequenced using standard techniques that are well-known in the art. Standard alignment programs and other bioinformatics tools that are well known in the art are used to align parts of the amplified DNA sequence with the known non-variable sequence for the mouse heavy chain. Based on this analysis, antigen binding residues that fall outside of the structural consensus regions but within the traditionally defined hyper-variable or complementarity-determining regions (CDRs) were identified. The identified CDRs did not align with the known mouse heavy chain sequence. Translation of these hypervariable sequences into protein provided identification of the amino acid sequence of the 3 CDRs on the heavy chain of FP-101.

The same methods were used to clone and sequence the light chains of FP-101, allowing identification of the 3 CDRs on the light chain. Together, these CDRs define the binding regions of antibodies that are capable of neutralizing hFSTL3 and which do not cross-react with Follistatin.

The same methods were used to clone and then sequence the heavy and light chains of FP-102, allowing for the identification of the CDRs and the binding regions of this antibody that is capable of neutralizing hFSTL3 and which does not cross-react with Follistatin.

The CDRs of anti-hFSTL3 antibodies displaying desirable characteristics (e.g., binding to hFSTL3 but not binding to hFST, exhibiting "neutralizing activity" against human FSTL3 binding to any of the test ligands) are shown in Table 1. The Heavy Chain Variable Region (HCVR) and Light Chain Variable Region (LCVR) amino acid sequences of certain anti-hFSTL3 antibodies displaying desirable characteristics (e.g., binding to hFSTL3 but not binding to hFST, exhibiting "neutralizing activity" against human FSTL3 binding to any of the test ligands) are shown in Table 2 and their corresponding nucleotide sequences are shown in Table 3.

TABLE 1

Complementarity-determining region (CDR) sequences from the FP-101 and FP-102 Antibodies

| CDR designation | Amino Acid Sequence | SEQ ID NO |
|---|---|---|
| CDRH1_FP101 | YSFTTYTMH | 3 |
| CDRH2_FP101 | WIGYIHPSSGYTDHI | 4 |
| CDRH3_FP101 | RLDYGY | 5 |
| CDRL1_FP101 | QSIVHSNGNTYLE | 8 |
| CDRL2_FP101 | LLIYKVSNRFS | 9 |
| CDRL3_FP101 | FQSSHIPP | 10 |
| CDRH1_FP102 | YTFTSYWMH | 13 |
| CDRH2_FP102 | WIGEINPGNGRTNY | 14 |
| CDRH3_FP102 | RWLLPRGPMDY | 15 |
| CDRL1_FP102 | QNVGTNVA | 18 |
| CDRL2_FP102 | GLIYSASYRYS | 19 |
| CDRL3_FP102 | QQYNSYPL | 20 |

TABLE 2

Variable region amino acid sequences from the FP-101 and FP-102 Antibodies

| Variable region desig-nation | Amino Acid Sequence | SEQ ID NO |
|---|---|---|
| HCVR_FP101 | EVQLQQSAAELARPGASVKMSCKASGYSFTT<br>YTMHWVKQRPGQGLEWIGYIHPSSGYTDHIQ<br>KFKDKTILTADKSSSTAYMQLNSLTSEDSAVY<br>YCARLDYGYWGQGTTLTVSSAKTTPPSVYPL<br>APGSAAQTNSMVTLGCLVKGYFPEPVTVTW<br>NSGSLSSGVHTFPAVLQSDLYTLSSSVTVPSST<br>WPSETVTCNVAHPASSTKVDKKIDYKDDDDK<br>FYSVT | 2 |
| LCVR_FP101 | DILMTQTPLSLPVSLGDQASISCRSSQSIVHSN<br>GNTYLEWYLQKPGQSPKLLIYKVSNRFSGVP<br>DRFTGSGSGTDFTLKISRVEAADLGVYYCFQS<br>SHIPPTFGGGTKLEIKRADAAPTVSIFPPSSEQ<br>LTSGGASVVCFLNNFYPKDINVKWKIDGSERQ<br>NGVLNSWTDQDSKDSTYSMSSTLTLTKDEYE<br>RHNSYTXEATHKTSTSPIVKSFN | 7 |
| HCVR_FP102 | MQVKLQQPGAELVKPGASVKLSCKASGYTFT<br>SYWMHWVNQRPGQGLEWIGEINPGNG<br>RTNYNEKFKSKATLTVDKSSSTAYMQLSSLTS<br>EDSAVYFCARWLLPRGPMDYWGQGTSVT<br>VSSAKTTPPSVYPLAPGSAAQTNSMVTLGCL<br>VKGYFPEPVTVTWNSGSLSSGVHTFPAVL<br>QSDLYTLSSSVTVPSSTWPSETVTCN | 12 |
| LCVR_FP102 | MDIVLTQSQKFMSTSVGDRVSVTCKASQNVG<br>TNVAWYQQKPGQSPQGLIYSASYRYSGVPDR<br>FTGSGSGTDFTLTISNVQSEDLAEYFCQQYNS | 17 |

TABLE 2-continued

Variable region amino acid sequences from the FP-101 and FP-102 Antibodies

| Variable region desig-nation | Amino Acid Sequence | SEQ ID NO |
|---|---|---|
| | YPLTFGAGTKLELKRADAAPTVSIFPPSSEQLT<br>SGGASVVCFLNNFYPKDINVKWKIDGSERQN<br>GVLNSWTDQDSKDSTYSMSSTLTLTKDEYER<br>HNSYTCEATHKTSTHP | |

TABLE 3

Variable region nucleotide sequences encoding variable regions of the FP-101 and FP-102 Antibodies

| Chain designation | Amino Acid Sequence | SEQ ID NO |
|---|---|---|
| HCVR_FP101_DNA | GAGGTTCAGCTGCAGCAGTCTGCAGCTGAA<br>CTGGCAAGACCTGGGGCCTCAGTGAAGATG<br>TCCTGCAAGGCTTCTGGCTACTCCTTTACAA<br>CCTACACGATGCACTGGGTAAAACAGAGGC<br>CTGGACAGGGTCTGGAATGGATTGGATACA<br>TTCATCCTAGCAGTGGATATACTGATCACAT<br>TCAGAAGTTCAAGGACAAGACCATATTGAC<br>TGCGGACAAATCCTCCAGCACAGCCTACAT<br>GCAACTGAACAGCCTAACATCTGAGGACTC<br>TGCGGTCTATTACTGTGCAAGATTGGACTAT<br>GGCTACTGGGGCCAAGGCACCACTCTCACA<br>GTCTCCTCAGCCAAAACGACACCCCCATCT<br>GTCTATCCACTGGCCCCTGGATCTGCTGCCC<br>AAACTAACTCCATGGTGACCCTGGGATGCC<br>TGGTCAAGGGCTATTTCCCTGAGCCAGTGA<br>CAGTGACCTGGAACTCTGGATCCCTGTCCA<br>GCGGTGTGCACACCTTCCCAGCTGTCCTGC<br>AGTCTGACCTCTACACTCTGAGCAGCTCAG<br>TGACTGTCCCCTCCAGCACCTGGCCCAGCG<br>AGACCGTCACCTGCAACGTTGCCCACCCGG<br>CCAGCAGCACCAAGGTGGACAAGAAAAN | 1 |
| LCVR_FP_101_DNA | ACTCAAACTCCACTCTCCCTGCCTGTCAGTC<br>TTGGAGATCAAGCCTCCATCTCTTGCAGATC<br>TAGTCAGAGCATTGTACATAGTAATGGAAA<br>CACCTATTTAGAATGGTACCTGCAGAAACC<br>AGGCCAGTCTCCAAAGCTCCTGATCTACAA<br>AGTTTCCAACCGATTTTCTGGGGTCCCAGAC<br>AGGTTCACTGGCAGTGGATCAGGGACAGAT<br>TTCACACTCAAGATCAGCAGAGTGGAGGCT<br>GCGGATCTGGGAGTTTATTACTGCTTTCAAA<br>GTTCACATATTCCTCCGACGTTCGGTGGAG<br>GCACCAAGCTGGAAATCAAACGGGCTGATG<br>CTGCACCAACTGTATCCATCTTCCCACCATC<br>CAGTGAGCAGTTAACATCTGGAGGTGCCTC<br>AGTCGTGTGCTTCTTGAACAACTTCTACCCC<br>AAAGACATCAATGTCAAGTGGAAGATTGAT<br>GGCAGTGAACGACAAAATGGCGTCCTGAAC<br>AGTTGGACTGATCAGGACAGCAAAGACAGC<br>ACCTACAGCATGAGCAGCACCCTCACGTTG<br>ACCAAGGACGAGTATGAACGACATAACAG<br>CTATACCNGTGAG | 6 |
| HCVR_FP102_DNA | ATGCAGGTTAAGCTGCAGCAGCCTGGGGCT<br>GAACTGGTGAAGCCTGGGGCTTCAGTGAAG<br>CTGTCCTGCAAGGCTTCTGGCTACACCTTCA<br>CCAGCTACTGGATGCACTGGGTGAATCAGA<br>GGCCTGGACAAGGCCTTGAGTGGATTGGAG<br>AGATTAATCCTGGCAACGGTCGTACTAACT<br>ACAATGAGAAGTTCAAGAGCAAGGCCACA<br>CTGACTGTAGACAAATCCTCCAGCACAGCC<br>TACATGCAACTCAGCAGCCTGACATCTGAG<br>GACTCTGCGGTCTATTTCTGCGCAAGATGGT<br>TGCTACCCCGGGGGCCTATGGACTACTGGG | 11 |

TABLE 3-continued Variable region nucleotide sequences encoding variable regions of the FP-101 and FP-102 Antibodies

| Chain designation | Amino Acid Sequence | SEQ ID NO |
|---|---|---|
| | GTCAAGGAACCTCAGTCACCGTCTCCTCAG<br>CCAAAACGACACCCCATCTGTCTATCCAC<br>TGGCCCCTGGATCTGCTGCCCAAACTAACT<br>CCATGGTGACCCTGGGATGCCTGGTCAAGG<br>GCTATTTCCCTGAGCCAGTGACAGTGACCT<br>GGAACTCTGGATCCCTGTCCAGCGGTGTGC<br>ACACCTTCCCAGCTGTCCTGCAGTCTGACCT<br>CTACACTCTGAGCAGCTCAGTGACTGTCCC<br>CTCCAGCACCTGGCCCAGCGAGACCGTCAC<br>CTGCAA | |
| LCVR_FP102_<br>DNA | ATGTCCACATCAGTAGGAGACAGGGTCAGC<br>GTCACCTGCAAGGCCAGTCAGAATGTGGGT<br>ACTAATGTAGCCTGGTATCAACAGAAACCA<br>GGGCAATCTCCTCAAGGACTGATTTACTCG<br>GCATCCTACCGGTACAGTGGAGTCCCTGAT<br>CGCTTCACAGGCAGTGGATCTGGGACAGAT<br>TTCACTCTCACCATCAGCAATGTGCAGTCTG<br>AAGACTTGGCAGAGTATTTCTGTCAGCAAT<br>ATAACAGCTATCCGCTCACGTTCGGTGCTG<br>GGACCAAGCTGGAGCTGAAACGGGCTGATG<br>CTGCACCAACTGTATCCATCTTCCCACCATC<br>CAGTGAGCAGTTAACATCTGGAGGTGCCTC<br>AGTCGTGTGCTTCTTGAACAACTTCTACCCC<br>AAAGACATCAATGTCAAGTGGAAGATTGAT<br>GGCAGTGAACGACAAAATGGCGTCCTGAAC<br>AGTTGGACTGATCAGGACAGCAAAGACAGC<br>ACCTACAGCATGAGCAGCACCCTCACGTTG<br>ACCAAGGACGAGTATGAACGACATAACAG<br>CTATACCTGTGAGGCCACTCACAAGACATC<br>AACTCACCCAT | 16 |

The same methods will be used to clone and then sequence the heavy and light chains of FP-103, allowing for the identification of the CDRs and the binding regions of this antibody that is Capable of Neutralizing hFSTL3 and which does not Cross-React with Follistatin.

Figure 8:
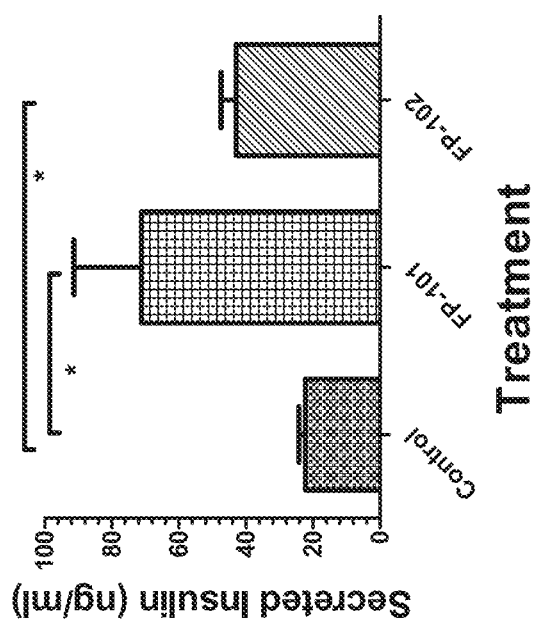
FIG. 8 shows the that FP-101 and FP-102 antibodies stimulate insulin release from mouse islets cultured for 24 hours. The antibodies enhance insulin secretion relative to the control antibody, an effect that would be beneficial to a patient with diabetes in which insulin production is insufficient to control blood glucose level.
Figure 9:
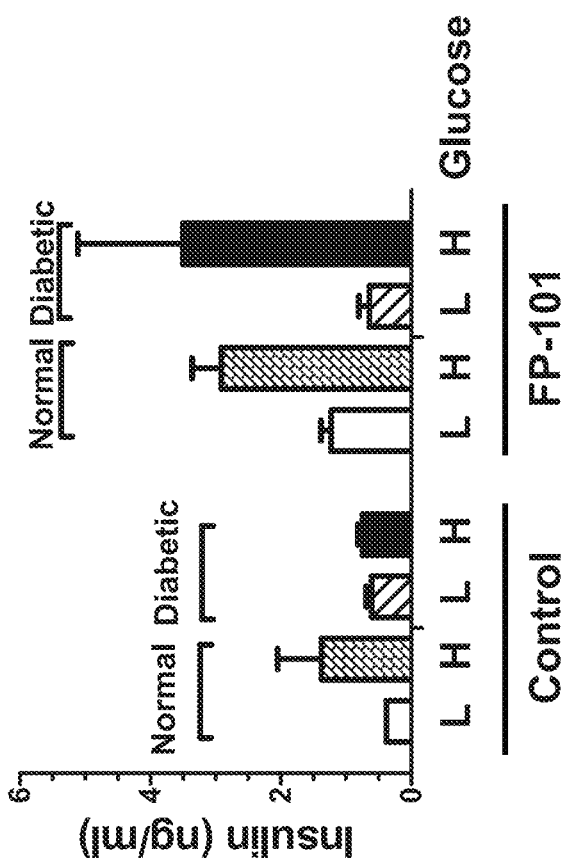
FIG. 9 shows FP-101 treatment restores glucose-stimulated insulin secretion from diabetic mouse islets. When no treatment was applied (control), normal islets secreted more insulin in high glucose compared to low (first 2 bars). Diabetic islets, however, did not increase insulin secretion in higher glucose (bars 3 and 4) which is typical for diabetic islets. In contrast, after treating islets with FP-101 for 24 hours, increased insulin release in high glucose similar to normal islets was observed (compare bars 7 and 8 to bars 3 and 4 and 5 and 6).

Example 6. Neutralization Activity of Anti-hFSTL3 Antibodies Demonstrated in Mouse Islets Islets were isolated from C57BL6 mice as previously described (Brown, M L et al Islets 3:367-75, 2011). After a 24-hour recovery period, culture medium was changed and 5 μg of each antibody or an equivalent volume of PBS for the control, was added and islets were cultured for an additional 24 hours. At the end of the culture, medium was removed and insulin secretion was determined using ELISA (Mercodia mouse insulin ELISA 10-1247-01). Results demonstrate that both FP-101 and FP-102 can significantly increase insulin release from beta cells in mouse islets, with FP-101 being approximately 2-fold better than FP-102 (FIG. 8). These results demonstrate that antibodies that neutralize FSTL3 can produce increased insulin release which would be beneficial as a treatment for diabetes, for example, where insulin is inadequate to control blood glucose levels.

Example 7. Engineered Anti-hFSTL3 Antibodies

Humanization of selected anti-hFSTL3 antibodies will be performed in order to reduce the apparent immunogenicity of the mouse-based antibodies. Using antibody engineering information well known in the art, and conventional bioinformatics tools, amino acid sequences of certain murine anti-hFSTL3 antibodies (e.g., FP-101, FP-102 and FP-103) of the invention will be analyzed and compared against known human antibody sequences. Based on these analyses and comparisons, certain human sequences will be chosen for conventional resurfacing, murine CDR grafting, and inclusion of suitable back mutations. In tests for binding to human FSTL3, these humanized antibodies will evaluated with respect to criteria such as affinity, avidity, binding kinetics, and biochemical behavior such as aggregation, as well as expression levels. These antibodies will be tested for cross reactivity to human Follistatin and will be optimized to minimize binding to human Follistatin protein. These antibodies will also be tested and optimized to exhibit optimal "neutralization activity" against human FSTL3 binding to any of the test ligands (e.g., activin A, activin B, GDF11 or myostatin ligands).

Example 8. Treatment of Islets with Anti-hFSTL3 Antibodies Restores and Enhances Glucose-Stimulated Insulin Secretion Mouse islets were isolated from normal or diabetic mice and cultured using standard conditions. Mice were made diabetic by feeding them a high fat diet for 1 week. The function of islets was tested using a standard glucose-stimulated insulin secretion (GSIS) test in which islets are cultured in low glucose for 1 hour and then moved to high glucose for 1 hour.

Human islets were cultured in low glucose, then moved to high glucose (standard GSIS test) to assess their function. Since obtaining islets from type 2 diabetic donors is quite rare, diabetes was simulated by first culturing the normal islets in high glucose for 24-48 hours, after which a standard GSIS test was performed.

Figure 10:
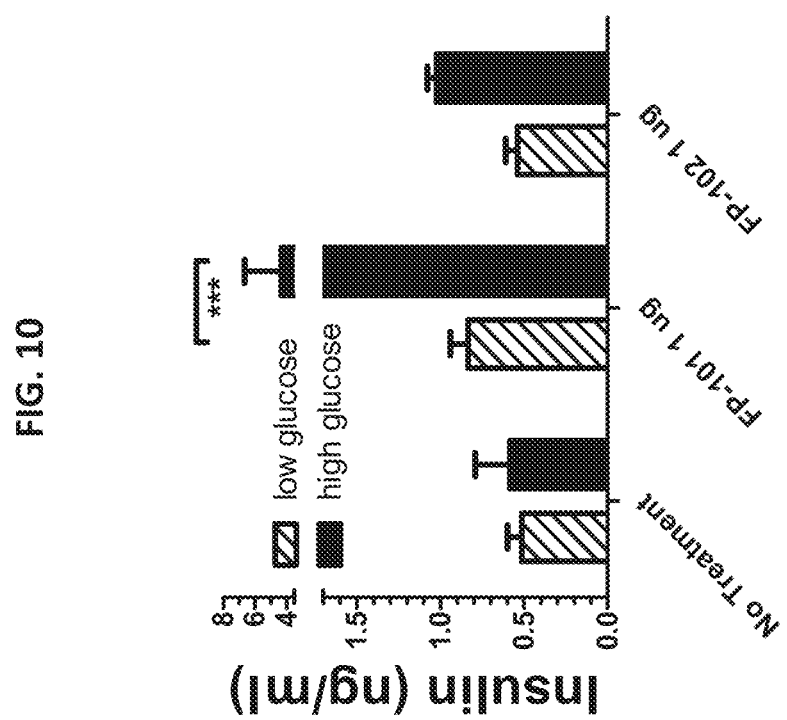
FIG. 10 shows FP-101 treatment restores glucose-stimulated insulin secretion in human islets. In the no treatment control (first 2 bars), there was no increase in insulin secretion when cultured in high glucose as would be observed in normal islets indicating that they are behaving like diabetic islets. Treatment with FP-101 restored elevated insulin secretion in high glucose so that diabetic islets now behave like normal islets. FP-102 tended to have the same effect but it was smaller, likely due to the reduced ability of FP-102 to neutralize FSTL3 compared to FP-101.

FP-101 treatment restored and enhanced glucose-stimulated insulin secretion from both diabetic mouse islets (FIG. 9) and human islets (FIG. 10) compared to no-treatment controls. In human islets, FP-102 tended to have the same effect but it was smaller, and likely due to the reduced ability of FP-102 to neutralize FSTL3 compared to FP-101 (FIG. 10). Treatment with FP-101 restored elevated insulin secretion in high glucose so that diabetic islets now behave like normal islets. These results demonstrate that the FSTL3 pathway is functional in human islets, as seen with mice (FIG. 9) and that inhibition of FSTL3 stimulates glucose-responsive insulin secretion in diabetic islets that would be beneficial in treating diabetic patients.

Example 9. Pharmacodynamics of mAb FP-101 in Mouse Serum after Intraperitoneal (IP) or Intravenous (IV) Injection Monoclonal antibody (mAb) FP-101 was injected by either IP or IV into normal mice at 10 mg/kg and the absorption and clearance of this antibody into blood was determined by taking blood samples at times indicated over 24 hours. To measure mAb in mouse blood, human FSTL3 was fixed onto 96-well plates. The mouse serum was diluted 1:10 with phosphate buffered saline (standard lab reagent) and 50 ul of this dilution was added. After 1-2 hours, the wells were washed and an enzyme-labeled anti-mouse antibody was added that binds to the mAb in the well.

Figure 11B:
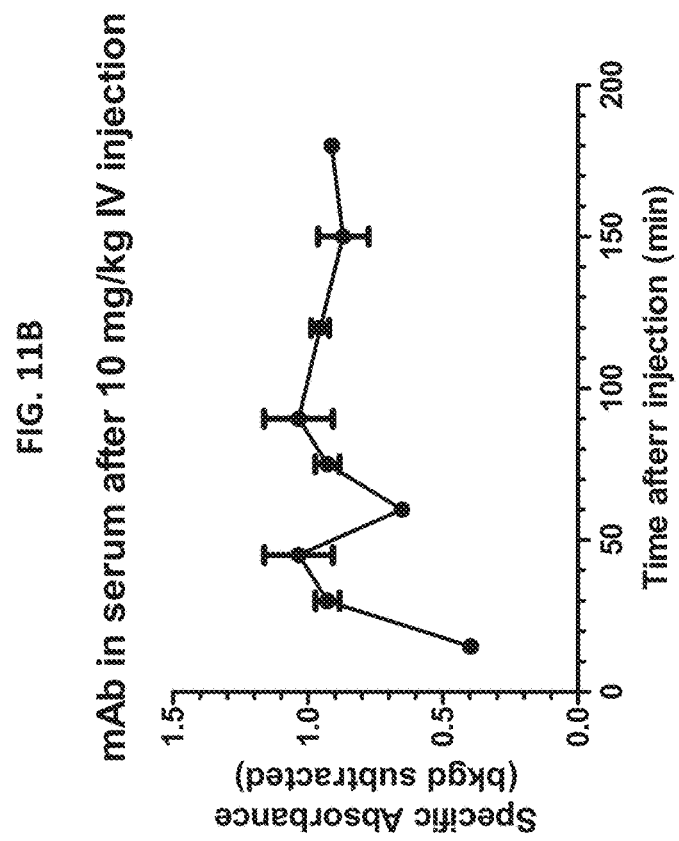
FIGS. 11A and 11B show pharmacodynamics of mAb FP-101 in mouse serum after intraperitoneal (IP) (FIG. 11A) or intravenous (IV) injection (FIG. 11B).
Figure 11A:
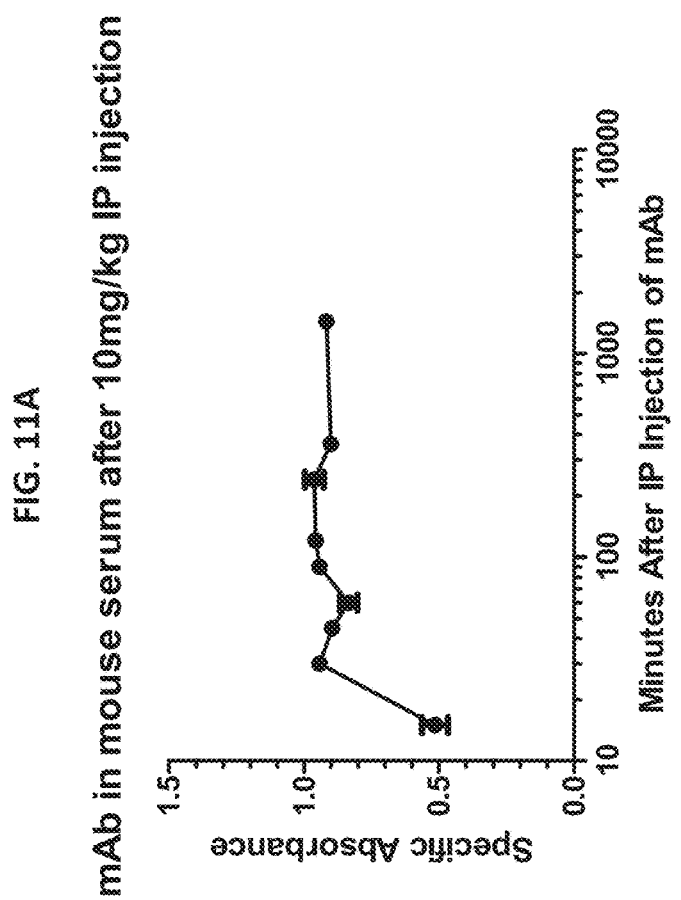

For IP administration, mAb was detected in all samples and the value didn't change suggesting fast absorption but slow clearance so that infrequent dosing of mAb can be effective in treating diabetes (FIG. 11A). Slow clearance of mAb was also detected upon IV administration, with mAb not changing significantly over 3 hours (FIG. 11B). These results indicate that FP-101 has a long half-life in mouse blood, a desirable characteristic for an antibody therapeutic.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An isolated antibody, or an antigen-binding fragment thereof, that binds to a human follistatin-like 3 (FSTL3) protein and neutralizes binding of FSTL3 to an FSTL3 ligand, wherein the antibody or antigen-binding fragment, comprises:
   (i) an antibody heavy chain variable ($V_H$) domain having:
      a) a CDR1 consisting of SEQ ID NO:3,
      c) a CDR2 consisting of SEQ ID NO:4, and
      e) a CDR3 consisting of SEQ ID NO:5,
   and
   (ii) an antibody variable light chain ($V_L$) domain having:
      g) a CDR1 consisting of SEQ ID NO:8,
      i) a CDR2 consisting of SEQ ID NO:9, and
      k) a CDR3 consisting of SEQ ID NO:10.

2. The antibody, or antigen-binding fragment, of claim 1, comprising an antibody heavy chain variable ($V_H$) domain comprising SEQ ID NO:2.

3. The antibody, or antigen-binding fragment, of claim 1, comprising an antibody variable light chain ($V_L$) domain comprising SEQ ID NO:7.

4. The antibody, or antigen-binding fragment, of claim 1, wherein the antibody is a humanized antibody.

5. The antibody, or antigen-binding fragment, of claim 1, wherein the antibody is a whole antibody.

6. The antibody, or antigen-binding fragment, of claim 1, wherein the antibody is an antigen-binding fragment of an antibody.

7. A composition comprising the antibody, or antigen-binding fragment, of claim 1, and a pharmaceutically-acceptable carrier.

8. A method of treating diabetes in a subject in need thereof, comprising administering to the subject an effective amount of an antibody, or an antigen-binding fragment thereof, that binds to a human follistatin-like 3 (FSTL3) protein, wherein the antibody or antigen-binding fragment, comprises:
   (i) an antibody heavy chain variable ($V_H$) domain having:
      a) a CDR1 consisting of SEQ ID NO:3,
      c) a CDR2 consisting of SEQ ID NO:4, and
      e) a CDR3 consisting of SEQ ID NO:5,
   and
   (ii) an antibody variable light chain ($V_L$) domain having:
      g) a CDR1 consisting of SEQ ID NO:8,
      i) a CDR2 consisting of SEQ ID NO:9, and
      k) a CDR3 consisting of SEQ ID NO:10.

9. The method of claim 8, comprising administering an effective amount of the antibody, or antigen-binding fragment thereof, to increase insulin secretion from a beta cell in the subject.

10. The method of claim 8, comprising administering an effective amount of the antibody, or antigen-binding fragment thereof, to increase beta cell regeneration in the subject.

11. The method of claim 8, comprising administering an effective amount of the antibody, or antigen-binding fragment thereof, to promote transdifferentiation of an alpha cell or other pancreatic cell to a beta cell in the subject.

12. The method of claim 8, comprising administering an effective amount of the antibody, or antigen-binding fragment thereof, to inhibit transdifferentiation of a beta cell to an alpha cell or other pancreatic cell in the subject.

13. The method of claim 8, wherein the subject has type 1 diabetes.

14. The method of claim 8, wherein the subject has type 2 diabetes.

* * * * *